United States Patent
Yu et al.

(10) Patent No.: US 8,855,738 B2
(45) Date of Patent: Oct. 7, 2014

(54) ACOUSTICALLY INDUCED BLOOD STASIS AND IN VIVO OPTICAL SPECTROSCOPY

(75) Inventors: Yan Yu, Rochester, NY (US); Brian Winey, Seneca Falls, NY (US); Lydia Liao, Rochester, NY (US)

(73) Assignee: University of Rochester, Rochester, NY (US)

( * ) Notice: Subject to any disclaimer, the term of this patent is extended or adjusted under 35 U.S.C. 154(b) by 573 days.

(21) Appl. No.: 11/505,492

(22) Filed: Aug. 17, 2006

(65) Prior Publication Data

US 2007/0055126 A1  Mar. 8, 2007

Related U.S. Application Data

(60) Provisional application No. 60/709,108, filed on Aug. 18, 2005.

(51) Int. Cl.
- *A61B 5/05* (2006.01)
- *A61B 5/00* (2006.01)
- *A61N 7/00* (2006.01)
- *A61B 8/08* (2006.01)
- *A61B 8/12* (2006.01)

(52) U.S. Cl.
CPC ............... *A61B 5/0086* (2013.01); *A61N 7/00* (2013.01); *A61B 5/0705* (2013.01); *A61B 8/0825* (2013.01); *A61B 8/12* (2013.01); *A61B 5/4381* (2013.01)
USPC ........................ 600/407; 600/473; 600/476

(58) Field of Classification Search
USPC ........................................ 600/407, 473, 476
See application file for complete search history.

(56) References Cited

U.S. PATENT DOCUMENTS

| | | | |
|---|---|---|---|
| 5,349,954 A * | 9/1994 | Tiemann et al. | 600/342 |
| 5,630,811 A * | 5/1997 | Miller | 606/9 |
| 5,762,609 A * | 6/1998 | Benaron et al. | 600/473 |
| 5,845,639 A * | 12/1998 | Hochman et al. | 600/407 |
| 6,002,958 A * | 12/1999 | Godik | 600/407 |
| 6,138,046 A * | 10/2000 | Dalton | 600/476 |
| 6,289,230 B1 * | 9/2001 | Chaiken et al. | 600/322 |
| 6,498,942 B1 * | 12/2002 | Esenaliev et al. | 600/310 |
| 2005/0033274 A1 * | 2/2005 | Pless et al. | 606/27 |
| 2006/0063995 A1 * | 3/2006 | Yodh et al. | 600/323 |

OTHER PUBLICATIONS

Esther L. Yuh, Suzanne G. Shulman, Shilpa A. Mehta, Jianwu Xie, Lili Chen, Victor Frenkel, Mark D. Bednarski, and King C. P. Li Delivery of Systemic Chemotherapeutic Agent to Tumors by Using Focused Ultrasound: Study in a Murine Model Radiology, Feb. 2005; 234: 431-437.*

Pretreatment oxygenation predicts radiation response in advanced squamous cell carcinoma of the head and neck. Nordsmark M, Overgaard M, Overgaard J. Radiother Oncol. Oct. 1996;41(1):31-9.*

(Continued)

*Primary Examiner* — Long V. Le
*Assistant Examiner* — Bo J Peng
(74) *Attorney, Agent, or Firm* — Cooper & Dunham LLP

(57) ABSTRACT

Ultrasound-induced blood stasis has been observed for more than thirty years. Most of the literature has been focused on the health risks associated with this phenomenon and methods employed to prevent stasis from occurring during ultrasound imaging. To date, experimental observations have been either in vitro or invasive. The current work demonstrates ultrasound-induced blood stasis in murine tumor and nontumor tissue, observed through noninvasive measurements of optical spectroscopy, and discusses possible diagnostic uses for this previously undesirable effect of ultrasound.

19 Claims, 21 Drawing Sheets

(56) References Cited

OTHER PUBLICATIONS

Stamatas et al., 2004, Blood stasis contributions to the perception of skin pigmentation, Journal of Biomedical Optics 9(2), 315-322 (Mar./Apr. 2004), p. 315-322.*

Arnold, Human Performance Effects of Decreased Cerebral Tissue Oxygen Saturation Induced by Various Levels of Mixed Oxygen/Nitrogen, Feb. 1995.*

Yuh, E.L. et al., Delivery of Systemic Chemotherapeutic Agent to Tumors by Using Focused Ultrasound: Study in a Murine Model. Radiology, Feb. 2005, vol. 234, pp. 431-437.

Nordsmark, M. et al., Pretreatment Oxygenation Predicts Radiation Response in Advanced Squamous Cell Carcinoma of the Head and Neck. Radiother. Oncol. Jul. 27, 1996, vol. 41, No. 1, pp. 31-39.

International Search Report in PCT/US06/32532, mailed May 3, 2007.

* cited by examiner

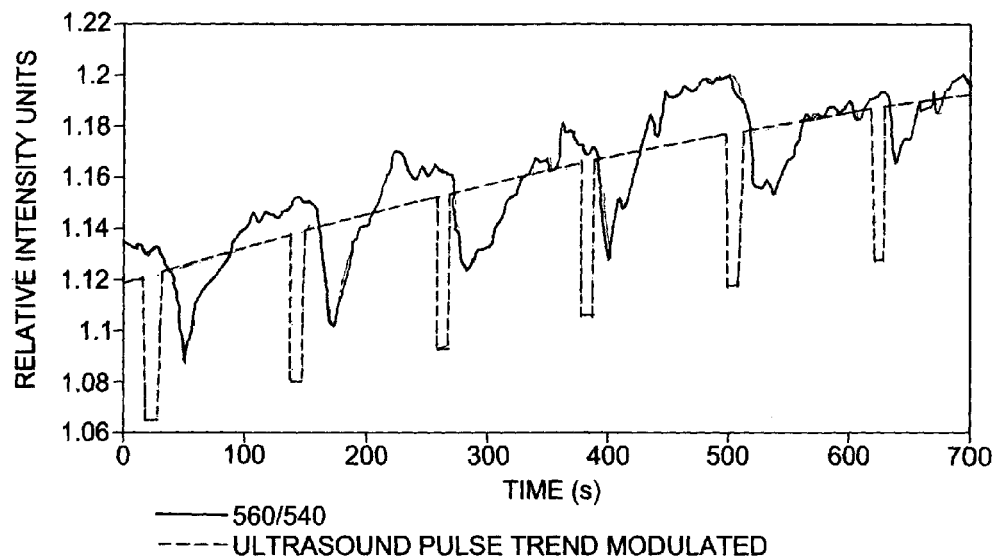
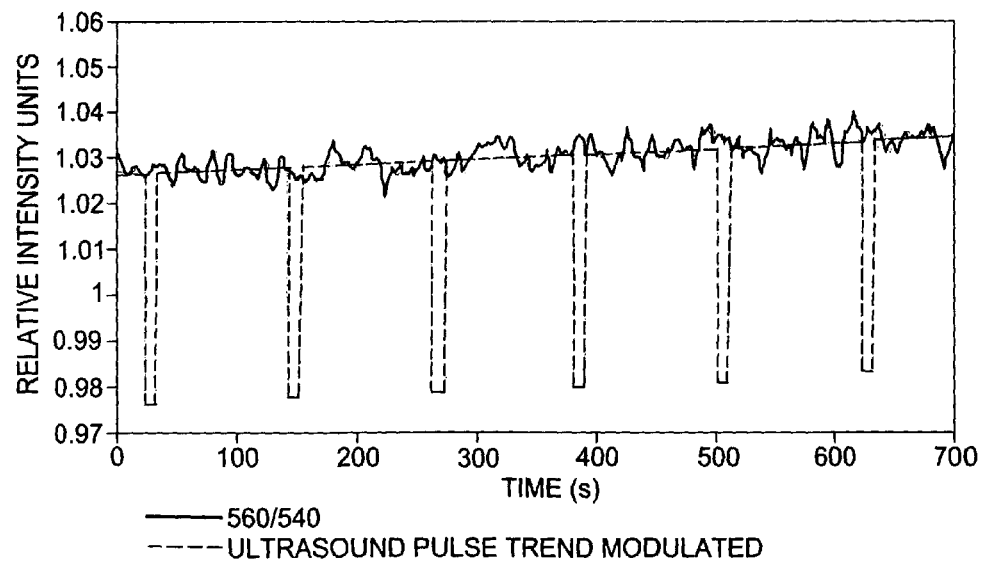

FIG. 12A       FIG. 12B
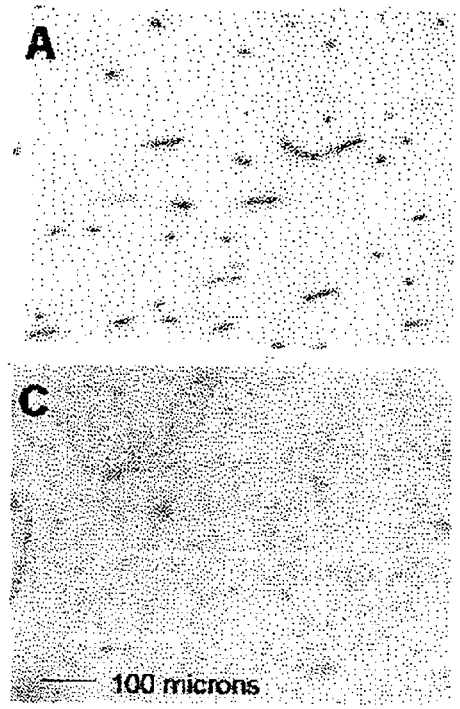 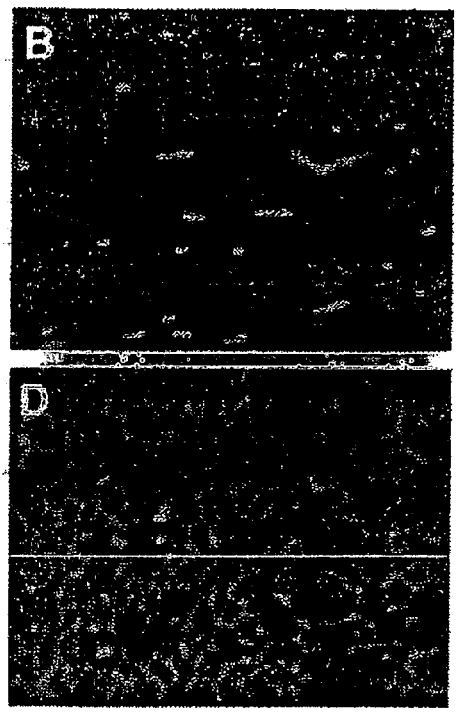
FIG. 12C       FIG. 12D

ACOUSTICALLY INDUCED BLOOD STASIS AND IN VIVO OPTICAL SPECTROSCOPY

REFERENCE TO RELATED APPLICATION

The present application claims the benefit of U.S. Provisional Patent Application No. 60/709,108, filed Aug. 18, 2005, whose disclosure is hereby incorporated by reference in its entirety into the present disclosure.

STATEMENT OF GOVERNMENT INTEREST

The work leading to the present invention was supported by National Cancer Institute Grant No. CA107860. The government has certain rights in the invention.

FIELD OF THE INVENTION

The present invention is directed to therapeutic and diagnostic techniques and more particularly to therapeutic and in vivo diagnostic techniques combining acoustically induced blood stasis with optical spectroscopy.

DESCRIPTION OF RELATED ART

Stationary sound waves have long been known to create banding effects when solids are suspended in liquids; sand in air (in a cylinder), bubbles in water, etc. Stationary ultrasound waves can create bands of red blood cells in vitro in chick embryos removed from the egg shell but kept alive in saline solution. The banding is due to the standing pressure wave created by the ultrasound. Even a traveling pressure wave, with small amounts of reflection at the tissue boundaries, can cause banding of blood cells in the plasma medium. Many have continued to study the diagnostic limits and dangers of ultrasound and ultrasound-induced stasis, but to the best of our knowledge, no one has investigated the diagnostic potential.

A limiting factor in studying this ultrasound-induced phenomenon has been the difficulty of measuring the blood flow alterations. Previous works have required the blood vessels to be dissected from the abdomen of mice or the removal of chick embryos from their shells so as to be seen with microscopes and stereoscopes. The phenomenon has only been observed invasively and only in a few vessels immediately on the tissue surface or in vessels separated from the surrounding tissue. Methods have been suggested to avoid prolonged blood stasis during diagnostic imaging and ultrasound intensity limits have been established to avoid tissue damage and to allow the blood flow to rebound. The current experiments have been conducted within the FDA therapeutic ultrasound limits (SPTA 0.720 mW/cm$^2$) and blood stasis and banding have been observed to be reversible under these conditions.

It has been shown that oxy and deoxyhemoglobin have signature absorption and scattering effects visible in steady-state broadband diffuse reflectance optical spectroscopy. Furthermore, oxyhemoglobin saturation can be determined using spectroscopic measurements of light reflected from tissue and analyzed with the diffusion approximation or the higher order P3 approximation. Spectral analysis performed with a P3 approximation fit has been shown to be sensitive to the dynamic changes of hemoglobin oxygen saturation due to changes in oxygen content of air being inhaled by mice.

Another topic of interest is ultrasound ablation. Ultrasound is currently being studied by several research groups as a tool for complete noninvasive tissue ablation. In general, the methods being studied employ a single focused transducer or an array of transducers capable of producing a variable distance focal point. The focused ultrasound is either swept through the tissue or operated in a burst mode at different burst durations and frequencies at high intensities with the outcome being a sudden localized temperature increase. The elevated temperatures are maintained for varying periods and frequencies, and cause cell death only in regions where the ultrasound is focused. The amount of temperature increase is proportional to the driving power of the transducer(s) and to the duration of the burst. For example, a 30 second burst of ultrasound produced by a single focused transducer driven by a 20 W signal can produce a temperature increase of 14 C. A full minute of sonication at the same power can produce an overall temperature increase of 30 C.

Cell death has been shown to occur when temperatures are elevated to temperatures above 41 C for extended periods of time, where 37 C is the ambient body temperature. A general rule is that for temperatures in the range of 43 C, a time of 150-240 minutes at the elevated temperature will cause complete cell death. The extensive range of times is due to various cell types and their respective abilities to survive higher temperature environments. For each degree above 43 C, the exposure time needed for complete cell death is halved. Another way to express this general rule is the following equation:

$$t_{43} = \sum_{t=0}^{t=final} 0.5^{(43-T)} \Delta t$$

where T is the temperature at time t measured over the interval $\Delta t$. The sum of this equation, $t_{43}$, is the time equivalent had the temperature remained at 43 C and a value greater than 240 minutes for $t_{43}$ implies almost certain complete cell death.

All published HIFU tissue ablation techniques rely upon a single transducer or array of transducers to produce a focused traveling wave acoustic field. The focus is located at 80, 90, 130, or 160 mm for the various designs and the focal spots were approximately 1 mm in diameter and 5 mm long. Regions of ablation were in the range of 4 mm in diameter and 7 mm long. The sonication times and intensities varied from device to device and from patient to patient. In general for the burst designs, pulses were between 10 and 20 seconds in duration and the intensity ranged from 28 W-50 W for one study and 100 W-400 W for another study. The studies employing a swept ultrasound focal zone employed higher intensities but the ultrasound was constantly moving at a rate of 1-3 mm/s.

Reports of previous studies are not in agreement regarding the intensity required for complete cell death in the region of ultrasound focus. Only half of the studies report temperature information for the tissue samples being sonicated. The sweeping ultrasound studies seem to employ extremely high intensities and do not record the temperature changes inside nor outside the focal zone. These studies simply record the pathological studies performed on the excised tissue. In those studies that do report temperature increases, the temperature increases range from 20 C-50 C for ten second pulses with about 50 second delays between subsequent sonications.

In general, the complete ablation of tissue samples of 1-2 cubic centimeters requires on average 2 hours of ultrasound treatment. All studies have reported patients complaining of pain, even when employing powers as low as 30 Watts. The present models require the patient to be lying on her stomach with the HIFU surgery device located below the breast with a lesion. This technique inhibits the treatment of tumors near the chest wall and is dangerous because of the exposure of the chest cavity to high intensity ultrasound.

SUMMARY OF THE INVENTION

It is an object of the invention to overcome the above-noted deficiencies of the prior art.

To that end, the present invention in at least one embodiment combines the above techniques, focused standing wave ultrasound-induced blood stasis and optical spectroscopy to develop a noninvasive imaging tool with potential use in tissue diagnostics.

Cells require a constant supply of oxygen for metabolic processes. Normally, as the cells consume oxygen, hemoglobin molecules in the blood continually replenish the oxygen supply as the blood flows through the vessels. When standing wave ultrasound is used to slow or stop the blood flow, the oxyhemoglobin saturation decreases as the available oxygen is depleted. When the blood flow is stopped or slowed for short periods of time, the oxyhemoglobin saturation can be observed to decrease, using optical spectroscopy measurements, and return to pre-ultrasound levels shortly after the ultrasound radiation is stopped.

The ultrasound intensities employed have been shown to create very little heating of the tissue and have not been shown to damage tissue. The pressures required to cause banding in moving blood are much lower than the intensities needed to deform the tissue of the heart.

The current experiments were designed to remain below tissue heating, tissue damage and tissue pressure thresholds and below the current FDA limits of diagnostic ultrasound intensities.

The invention has been experimentally verified. As hypothesized, the phenomenon of acoustic contrast due to blood flow stasis was clearly shown in the near infrared (NIR) spectral region. There were marked differences in the response of tumor vs. normal tissue to this acoustic contrast in the mouse model, to the extent that a simple analytical discriminator can achieve diagnostic accuracy of 0.90 for the area under the receiver-operating characteristics (ROC) curves. Sono-contrast NIR measurements are quantitatively predictive of the immunohistochemical measurement of blood vessel morphology in regression analysis at $p<0.01$.

The blood flow arrestment can be used to advantage in normal tissue by sparing it regionally from harmful interventions such as radiation or other temporal therapies. Of course this does not need optical spectroscopy, but rather is based on the general principle that ultrasound when used to arrest blood flow temporarily may be employed as an adjuvant to protect normal tissue as well as expose diseased tissue to therapeutics. Along the same thought, it is not necessary to employ optical spectroscopy: any technique that is sensitive to changes in blood flow or concentration will be able to detect the difference in effect caused by ultrasound in different tissue types (e.g., diseased vs. healthy).

Also, it is possible to use ultrasound and infrared spectroscopy for the detection, diagnosis, characterization and localization of cancers inside the body, such as the prostate or cervix. One approach is to administer ultrasound from outside the body or through a bodily cavity (such as the rectum), and interrogate infrared imaging through another bodily cavity (such as the urethra) via a 360 degree or rotating light source/collection fiber assembly, which may contain a plurality of active interrogation depths along the assembly for 3-dimensional imaging. It uses the same principle of creating spectral contrast via focal ultrasound, but the design of the instrumentation is different from that of exposed solid organs. Two possible configurations will be described in greater detail below, where the focal ultrasound is administered either trans-rectally or trans-abdominally.

Three variations of the invention will now be discussed. For such variations, it is sometimes desirable to operate the device in a high magnetic field or high radiation field setting, which requires (a) isolation of instrumentation into in-field and out-of-field (remote) subsystems, and (b) magnetic compatibility or radiation resistance for the in-field instrumentation.

The first variation involves high intensity focused ultrasound for ablation of benign or malignant masses in the breast or other soft tissues. There is a lack of FDA approved high intensity focused ultrasound (HIFU) system for the ablation of benign or malignant solid masses in the breast. One HIFU manufacturer, Haifu (based in Chongqing, China), currently dominates the world market by virtue of having a large base of clinical experience primarily from clinical trials in China. Several research groups in the U.S. are collaborating with Haifu to conduct trials that are designed to support FDA approval of this system in the U.S. market. This device is bulky, expensive, and uses MRI for guidance and temperature monitoring (see, for example, http://www.hifutech.com/ and http://www.medica.de/cipp/md_medica/custom/pub/content,lang,2/oid,17541/ticket,g_u_e_s_t). Although it is multipurpose, the size, expense and complexity of the system do not warrant widespread use of common diseases found in the U.S., such as fibroadenomas, high risk lesions such as atypical ductal or lobular hyperplasia, papilloma, fibromatosis, papillomatosis, and clinically confined cancers of the breast.

For example, fibroadenoma is a benign condition of the breast, which often leads to surgical removal in the operating room due to patient discomfort and clinical concern (if imaging findings indicate interval growth). There is no risk of disease spread if the original fibroadenoma is not completed excised, therefore it is an excellent candidate for more conservative treatments, such as in vivo image-guided ablation. Regarding breast cancers in the U.S. and western countries, widespread screening programs, genetic assays, improved diagnostic tools such as compound ultrasound, dynamic contrast enhanced MRI and large core needle biopsy have continually led to early diagnosis, with tumor size often below 1 cm. For such small tumors, traditional lumpectomy under rudimentary (wire localization) guidance in open surgery is both overly invasive and inefficient. Thus there is a need to develop a technology-enabled, image-guided, minimally invasive method to ablate a well-circumscribed mass in the breast, ultimately operating in an outpatient or office setting, and being available to all community, healthcare environments.

The present invention can address the above stated needs effectively. It is proposed to use two ultrasonic transducers driven by an external amplifier capable of therapeutic power delivery, with the ultrasonic beams intersecting at an angle such as 90 degrees, which in turn defines the region of HIFU. This region is first visualized by such means as a diagnostic ultrasound probe positioned through the central axis, and its tissue characteristics may be interrogated via optical spectroscopy (as disclosed below with regard to the third variation).

Temperature monitoring in the presence of blood flow and tissue heterogeneity is a known challenge in HIFU. We employ a simple solution for the breast by inserting tiny temperature measuring semiconductor probes (thermistors)

interstitially in and around the mass to be ablated. Digital readout and feedback control are possible to ensure adequate but safe ablation power.

In addition to ultrasound guidance, it is conceptually simple to integrate MRI guidance when the present invention is separated into the in-room, magnetically compatible subsystem and the remote (out-of-field) subsystem. Co-registration of image space between MRI and the present invention is achieved by imaging MRI fiducial points at known locations in the present system. Co-registration of MRI and ultrasound image spaces can be achieved similarly. Use of MRI for guidance may be advantageous in some cases, because dynamic contrast enhanced MRI is best for delineating the extent of cancerous disease in the breast at this time.

Our design and protocol aim to lower the intensity required for tissue ablation, increase access to more tumors in the breast, eliminate pain and discomfort from extreme high intensity ultrasound, reduce the risk of damaging tissue along the beam path and on the tissue surface, decrease the danger of exposing the chest cavity to acoustic radiation, and decrease the treatment time.

The chief difference between previous systems and the present proposed system, is the use of a plurality of transducers, e.g., dual 1 MHz transducers, capable of producing a single standing wave in the region where the two corresponding focal zones overlap. The system being proposed allows for the patient to remain seated during the entire treatment. The benefits of using two transducers are reduced power needed for the individual acoustic fields, isolated and localized high intensity region, and a preconfigured geometry for a precisely known high intensity focal volume eliminating the need for pretreatment location calibration.

All current clinical models rely upon a single transducer model using MRI to monitor the heating and location of the high intensity focal zone. The present design will not require the time and expense of MRI correlation. The focal zone will be known precisely due to the geometry of the dual transducers. Temperatures can be measured using a simple fiber array capable of measuring IR heat waves. Additionally, the present system will be equipped with a secondary ultrasound imaging system which can measure tissue ablation due to the change in tissue elasticity and deformability after ablation.

The second variation involves focused ultrasound for manipulation of tissue oxygenation to aid radiotherapy. Radiation therapy for cell kill relies on the presence of oxygen. Normal tissues are well oxygenated in a steady state, whereas tumor tissues can be either hypoxic when the mass is large, or inefficiently oxygenated due to malformed blood vessels. As explained above, focused ultrasound can be used to manipulate blood flow and tissue oxygenation in a murine model. Another embodiment aids radiotherapy of human cancers either immediately prior to or during administration of radiation therapy. As will be shown below, the ultimate aim is to (a) enhance the therapeutic ratio of tumor kill vs. normal tissue sparing, (b) shorten the course of fractionated radiotherapy from the typical 5-8 weeks to 1 hr-5 days.

In conventional radiotherapy, the radiation kills tumor cells up to the point where only hypoxic cells are left intact because of lack of oxygen. These hypoxic cells then re-oxygenate as the tumor burden decreases and the hypoxic region is exposed. For this reason, radiation is typically delivered in fractions, usually one fraction per day, 5 fractions per week, and lasts for 5-8 weeks for a definitive course of therapy. (Of course, tumor continues to grow over the weekend, but radiotherapy is rarely administered on Saturdays and Sundays.) Many patients desire a short course of radiation, ideally a single fraction, or at least one week of treatment instead of many weeks. This is why treatment techniques such as MammoSite and seed implant brachytherapy are popular. Using the present invention, it is possible to re-oxygenate the tumor volume prior to, during or immediately after a period of radiation delivery, via such mechanisms as reactive hyperemia from focused ultrasound. For example, focused ultrasound can be directed at the tumor cavity when the patient is positioned for treatment of breast cancer using modern, computer-controlled linear accelerator. After a pre-determined dose is delivered, the radiation is switched off, and the ultrasound pulse is activated briefly to manipulate blood flow in the region in a fashion to accelerate re-oxygenation, thus shortening the requirement for fractionation from one fraction per day to approximately 50 sec. per fraction. This is the principle on which a new era of radiation treatment of cancers via rapid fractionation is based.

Another aim in radiotherapy is to spare normal tissues surrounding the tumor target volume. Normal tissues are usually well perfused, i.e., susceptible to radiation damage due to availability of oxygen. Thus there is a reverse therapeutic ratio, i.e., tumor cells will be protected while normal cells will be killed, in single fraction radiation. This is another rationale for the need of prolonged fractionation schemes. The present invention allows use of focused ultrasound to suppress blood flow and thus protect normal tissues during radiation delivery. This is achieved by directing the focused ultrasound geographically at the in-field normal tissue volume in coordination with beam-on control of the linear accelerator, so that oxygen is temporarily depleted in healthy tissue when the radiation is switched on. Therefore, the present invention eliminates the undesirable reverse therapeutic ratio and in fact creates an advantageous therapeutic ratio (sparing normal tissue while achieving cell kill) in a single fraction or small number of fractions.

There are several radiation enhancing agents under intense research study. These include antiangiogenic agents, Cox-2 inhibitors, all of which are administered systemically, i.e., with no geographic advantage in terms of tumor vs. normal tissues. In contrast, the present invention provides radiation enhancement to tumor and sparing of normal tissues by both mechanisms of oxygenation and geographic aim. Through this combination, it is envisioned that a therapeutic dose can be delivered in a matter of 1 hr without the need to move the patient.

Detailed workflow of rapid fractionation is outlined as follows:

1. Clinician defines the tumor and planning targeting volume on CT, MRI, PET etc.
2. Radiation dosimetry plan is generated by medical physicist/dosimetrist.
3. Focused ultrasound array configuration planning is generated by medical physicist/dosimetrist based on the radiation dosimetry plan with the goal of sparing in-field normal tissue and oxygenating the central necrotic mass of the tumor volume.
4. Patient is positioned in the treatment room.
5. Radiation generating machine is moved to the correct configuration for each field to be delivered.
6. Focused ultrasound configuration is moved to the corresponding position for sparing normal tissue traversed by the given radiation beam; focal ultrasound directed at the tumor may or may not need to be moved, depending on if the instrumentation is in the path of the radiation beam.
7. Oxy- and deoxy-hemoglobin levels can optionally be monitored by the optical spectroscopy technique as disclosed below with regard to the third variation.

8. Focal ultrasound is switched on to achieve depletion of normal tissue oxygenation; radiation beam is switched on.

9. Radiation beam is switched off; focal ultrasound is switched on to oxygenate the tumor mass; allow sufficient time for oxygenation of tumor mass.

10. Repeat steps 8-9 above if necessary for the given radiation beam angles.

11. Radiation generating machine is configured for the next beam; repeat steps 6-10 above, until all beams are delivered to the full dose.

The third variation involves diagnosis, monitoring of therapeutic effectiveness, and treatment follow-up of cancers of the breast and other soft tissues. We have designed a scanhead capable of delivering focused acoustic stationary fields up to 4 cm deep in the tissue. The two 1 MHz focused transducers are aligned in a single plane at 90 degrees. The focal zone is approximately 1 cm in diameter and, with a 5 second exposure, can be shown to successfully stop blood flow. The field intensity is within the FDA diagnostic limit and generates less than 1 C local temperature increase.

The scanhead also incorporated a fiber array. The fiber array is connected to a dual wavelength diode light source (680 and 830 nm; other wavelengths are also possible) which is split into 9 fibers placed on the surface of the tissue with the scanhead. The collection fibers are combined into a single fiber which terminates at a room temperature spectroscope. The collection fibers can be separated and the sources intensity modulated for diffuse optical imaging.

The final component of the scanhead is a commercial ultrasound probe. The ultrasound probe is located in the same plane as the focused transducers and is used for image coregistration with the near infrared spectroscopy information, tissue density information and blood flow information.

The scanhead is designed to be gently placed upon the surface of the skin, above the tumor or questionable tissue. This information is gathered with a pre-scan ultrasound or mammogram. After the scanhead is placed on the surface of the skin, the optical data collection is begun. From this point to the conclusion of the exam, the scanhead is not moved. Any motion of the tissue or the scanhead will destroy image correlation.

In order to minimize motion of the scanhead, the ultrasound probe and focused transducers are given two degrees of freedom (DOF) within the scanhead in order for the focal zone to be positioned at various depths and lateral locations with respect to the tumor. This will generate a two dimensional map of the tissue surrounding and including the questionable tissue sample.

To use this system for diagnosis, monitoring of disease, progression or remission, the following steps are envisioned:

1. Position scanhead on patient at convenient angle; fix all scanhead support joints.

2. Use diagnostic ultrasound probe to verify alignment of focal center; move assembly axially away from or near patient's skin if necessary, so as to aim at desired depth in vivo.

3. Acquire baseline optical information.

4. Switch on focal ultrasound; acquire optical information.

5. Switch off focal ultrasound; acquire optical information.

6. Repeat steps 4-5 if necessary, allowing adequate interval in between.

7. To scan laterally, move assembly to left or right by manual or motorized actuation.

8. To scan depth-wise, move assembly axially away from or near patient.

9. To construct 2D imaging representation of data, scan in both directions.

10. To construct 3D image volume, it is necessary to scan adjacent planes or radially.

BRIEF DESCRIPTION OF THE DRAWINGS

Preferred embodiments will be set forth in detail with reference to the drawings, in which:

FIG. 2A shows the ratio $I_{560}/I_{540}$ signal with the trend modulated ultrasound signal superimposed for a typical non-tumor tissue;

FIG. 2B shows the same for a typical tumor tissue;

FIGS. 12A-12D show an immunohistochemistry analysis;

DETAILED DESCRIPTION OF THE PREFERRED EMBODIMENTS

Figure 1:
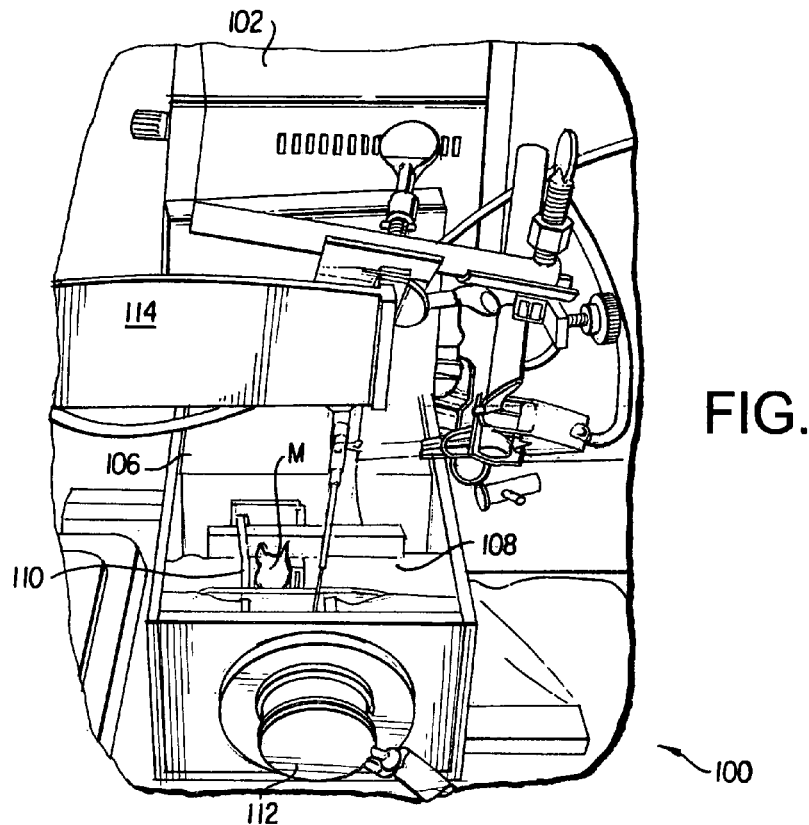
FIG. 1 shows an experimental test setup according to the first preferred embodiment.

Preferred embodiments of the present invention will be set forth in detail with reference to the drawings, in which like reference numerals refer to like elements or steps throughout.

FIG. 1 shows an apparatus 100 according to the first preferred embodiment. The apparatus 100 includes a heater 102, a rubber absorber 104, an optical probe 106, a metal reflector 108, a Plexiglas restraint 110 for restraining a test subject (mouse) M, an ultrasound transducer 112, a positioning arm 114, and a Plexiglas water tank 116.

Ultrasound was generated by a ≈1 MHz piezoelectric ceramic crystal (Channel Industries) mounted behind a concave aluminum lens with a focal length of 7 cm. At 1 MHz the −6 dB focal zone diameter was 2 mm and the focal zone length was 30 mm. The ultrasound signal was created by a function generator (Agilent 33250A) and amplified by an RF amplifier (Amplifier Research 25A250A), monitored and recorded by an oscilloscope (Tektronix TDS 2022). The ultrasonic field was measured and characterized using a hydrophone (Onda Co. HNR 500). The intensity of the ultrasound was maintained at Spatial Peak Temporal Average Intensity (SPTA)≈0.7 mW/cm$^2$, averaged over the burst cycle.

Initial tests of the ultrasound setup included a repeat of Dyson's seminal experiment (M. Dyson et al, "The flow of red blood cells stopped by ultrasound," Nature, Vol. 232, pp. 572-573, 1971), but with lower acoustic intensities (SPTA=0.7 mW/cm$^2$) and lower frequencies (f≈1 MHz). The ultrasound was observed visually to stop blood flow, causing bands to form for short periods of time. In order to perform a non-invasive test regarding the efficacy of the ultrasound in the mouse leg, a laser Doppler system (Transonic BLF21) was used to verify blood flow alterations or stasis due to ultrasound. This technique relies on the interference between an LED signal beam and the reflected beam, revealing the velocity profiles of the reflecting objects visualized as sidebands to the original beam, From the laser Doppler measurements, it is clear that in a small target volume the average velocity of the blood is at least slowing. When this same volume element is inspected with white light, there are measurable changes in the oxyhemoglobin saturation.

All experiments were conducted in a Plexiglas water tank 116. Distilled water was autoclaved for 45 minutes to remove ions and micro-bubbles in order to prevent cavitation and scattering of the acoustic field. A 2.5 cm thick piece of aluminum was used for the acoustic reflector 108, and a 2.5 cm thick rubber block 104 was placed behind the aluminum to absorb any scattered acoustic energy. During experiments, the water was heated to 37° C. using a circulating water heater 102, and the rubber block 104 was positioned to shield the data collection area from most of the water currents, since moving water can interfere with spectroscopy measurements.

Diffuse reflectance spectra were collected with a single 600 micron fiber, numerical aperture (N.A.)≈0.22, residing at the center of a seven fiber probe 106 (Ocean Optics, R600-7-VIS/NIR). The center collection fiber was connected to a 2048 pixel room temperature spectrometer (Ocean Optics, USB 2000-VIS/NIR) fitted with a grating for spectrum analysis between 200 nm and 1100 nm. The outer six fibers were connected to a broadband halogen light source (Ocean Optics, HL 2000). The source detector separation was 1 mm, resulting in an inspection volume of ≈9 mm$^3$, mostly within 1 mm of the tissue surface. The optical signal was weighted by the intensity curve of the light source. The intensity curvature was measured with a diffuse reflectance standard.

Six-eight week old C3H mice were inoculated intramuscularly to the right thigh with 10$^6$ MCa-35 mammary carcinoma cells, with the left hind leg used as control for the diagnostic portion of this experiment. To avoid scattering of the acoustic field, hair was removed from the hind legs using a depilatory agent (Nair®) one day prior to the experiment. The mice were sedated using a Ketamine (60 mg/kg) Xylazine (4 mg/kg) mixture injected intraperitoneally and placed in a Plexiglas restraint which positioned the leg to be examined away from the body. The probe was then fixed on the skin of the mouse leg using a positioning arm, ensuring contact but without skin compression. During data collection, the probe was held stationary, maintaining a constant pressure on the mouse skin. Optical spectroscopy measurements of hemoglobin in vivo are greatly dependent upon surface pressure since any changes will alter the blood volume alterations and consequently, hemoglobin volumes. Once a baseline spectrum was achieved (≈4 minutes), the mouse/probe were moved such that the focus of the ultrasound was ≈2 mm directly under the location of the optical probe. The direction of propagation of the ultrasound and light were kept orthogonal so that the metallic probe did not enter the focus of the ultrasound and obstruct or scatter the standing acoustic wave. Also, this increased the probability of intersecting the acoustic focal region with the volume of optical inspection.

During each experiment, ultrasound was administered in 5-second bursts, with 55-second relaxation periods between bursts and a total of six bursts per leg per experimental collection. For each mouse, both legs, one with a tumor (diameter≈10 mm) and one without, were subjected to ultrasound and optical spectroscopy to compare the effects in tumor versus nontumor tissue. The order of inspection of the legs was altered to diminish the possibility that the results were influenced by the depth of the anesthesia, which can directly affect the blood velocity.

Ultrasound pulse information for each experiment was monitored and collected with the oscilloscope and stored for later signal correlation studies, Optical spectra were collected with the supplied Ocean Optics software at 500 ms intervals in order to decrease the Signal to Noise Ratio (SNR) and to reduce the appearance of unwanted higher frequency signals and noise.

The raw optical spectra were corrected for the curvature of the light source intensity. The intensity curve of the light source was obtained using a diffuse reflectance standard. The optical signal then was cropped to avoid the spectral regions of low light (<400 nm) and regions near the end of the spectrometer's sensitivity (>1000 nm). Ultimately, the spectra were cropped to regions between 475 nm and 650 nm where significant changes in optical absorption are present due to oxy/deoxyhemoglobin shifts and few other absorbers affect this region of the spectrum. Several isolated wavelengths were initially considered (515 nm, 528 nm, 540 nm, 560 nm, 579 nm and 578 nm), but eventually the ratio of intensities (I) at two wavelengths, 560 nm and 540 nm, was chosen, The ratio of $I_{560}/I_{540}$ has been shown to be significantly affected by the presence (or absence) of the ultrasound. Since the intensities at 560 nm and 540 nm are dependent upon the oxy/deoxyhemoglobin saturations, it can be demonstrated that the ratio $I_{560}/I_{540}$ correlates to oxyhemoglobin concentrations.

Figure 3:
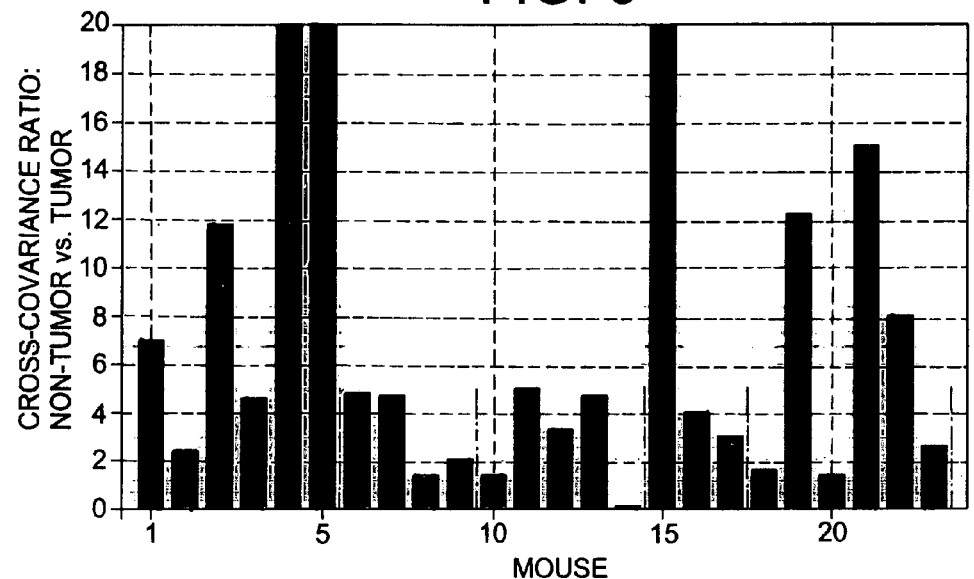
FIG. 3 shows a cross co-variance ratio for non-tumor vs. tumor.

By visual comparison of $I_{560}/I_{540}$ with the ultrasound signal, one can generally establish visual temporal correlation between these two signals in the non-tumor scans and the absence of correlation in the tumor scans. FIGS. 2A and 2B show, respectively, the ratio $I_{560}/I_{540}$ signal with the trend modulated ultrasound pulse signal superimposed for a typical nontumor tissue and tumor tissue. Notice the much larger ultrasound induced contrast in the nontumor signal. The drops in the $I_{560}/I_{540}$ ratio signal have been consistently observed in nontumor scans and are mostly absent in tumor scans. It has been demonstrated since that the mathematical correlation between the ratio signal and the ultrasound signal in general is significantly higher in nontumor cases than in tumor cases. As shown in FIG. 3, the $I_{560}/I_{540}$ signal in nontumor tissue is better correlated to the ultrasound than the same signal for tumor tissue, measured for the same mouse to compensate for differences in mice population.

Figure 4:
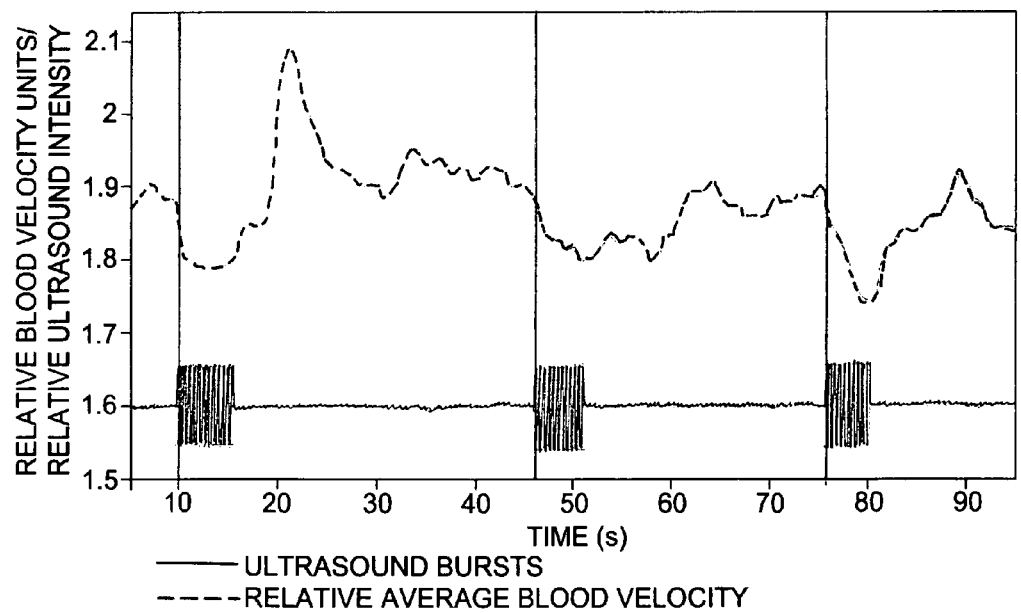
FIG. 4 shows a laser Doppler relative average volume velocity and ultrasound bursts.

As predicted from prior studies, the presence of the standing wave ultrasound caused changes in the blood flow, and, consequently, changes in the hemoglobin concentrations. These changes in the hemoglobin concentration affected optical absorption and the experimental spectroscopic measurements demonstrated this phenomenon. In FIG. 4, the top curve represents the laser Doppler average volume velocity, while the bottom curve represents the ultrasound bursts.

These changes in oxy/deoxyhemoglobin concentration are believed to be caused by metabolic consumption of oxygen. The rate of metabolic consumption varies from mouse to mouse and from tumor to nontumor tissue types. It is generally believed that tumor cells have higher metabolic rates and therefore consume more oxygen in relation to nontumor tissue. This alone would lead one to expect that oxyhemoglobin concentrations would drop faster and more emphatically in tumor tissue than in nontumor tissue. In general, such drops were not observed in our experiment, although, in some instances tumor tissue did exhibit oxyhemoglobin drops when the optical probe was located in close proximity to visible (large) surface vessels. In these cases, higher initial oxyhemoglobin concentrations were also observed and the ultrasound-induced contrast was visible in the measured ratio signal. When the probe was carefully moved to a location distant (1-2 mm) from the visible vessel, the initial oxyhemoglobin concentration dropped and the contrast was much less pronounced. The ultrasound-induced contrast was much less dependent upon location in the nontumor leg.

Initial tumor and nontumor tissue oxyhemoglobin concentrations varied from mouse to mouse, probably due to the depth of the anesthesia. Some mice with higher initial oxyhemoglobin concentrations demonstrated ultrasound-induced contrast in the tumor tissue. This contrast however was generally less substantial than the contrast observed in the nontumor tissue of the same mouse. Comparison of the ultrasound-induced contrast of each leg to the other leg of the same mouse was a technique used to reduce the mouse-to-mouse variance of oxyhemoglobin saturation. There are significant differences in the diffuse reflectance spectra gathered from different mice and from various locations of a single tumor in each mouse.

For each mouse, the difference in ultrasound-induced oxyhemoglobin concentration changes between tumor and nontumor tissue could result from differences in blood vessel counts and vessel orientation within the tissue, as well as differences in the metabolic rates of each tissue. The MCa-35 tumor is a highly vascularized, well perfused metastatic model and develops an extremely chaotic mesh of blood vessels; it is generally well oxygenated when compared to other tumor species models. When these tumors were analyzed with laser Doppler, the ultrasound appeared to have little effect on the blood flow, possibly due to the multidirectional and interwoven mesh of blood vessels which lack the orderly flow of skeletal vessels. In addition, the tumors generally had lower initial oxyhemoglobin saturations than the nontumor tissue of the other leg. Alternative tumor models with lower oxygenation, fewer vessels, and decreased blood flow ultrasound.

In general, the ultrasound-induced contrast was much more pronounced when initial hemoglobin concentrations were elevated. This elevation could be due to inflammation of the skin, abrasion, higher vessel counts, large vessels in close proximity to the probe, less pressure exerted by the probe on the skin, etc. Although, experimental procedures attempted to decrease the effects of inflammation, abrasion, and probe force on the skin, it was unclear which factor predominated in producing the varying spectral responses between mice. Additional studies are needed to further investigate these factors.

Figure 5:
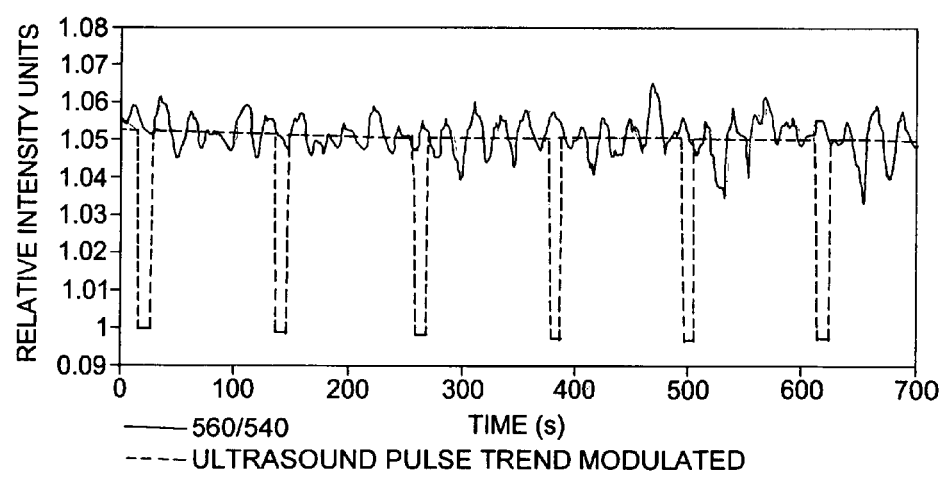
FIG. 5 shows the $I_{506}/I_{540}$ ratio signal for non-tumor tissue with the trend modulated ultrasound pulse superimposed.

Decreases in the observed $I_{560}/I_{540}$ ratios were predictable, generally corresponding to the ultrasound bursts, but not always easily observable. FIG. 5 shows the $I_{560}/I_{540}$ ratio signal for non-tumor signal with the trend modulated ultrasound pulse superimposed. The ultrasound-induced drops are difficult to distinguish. In some experiments it was hard to distinguish between responses of tumor and nontumor tissue. If the probe was positioned in the proximity of a major blood vessel in the tumor, the observed signal behaved in a manner similar to the nontumor cases (i.e., substantial decreases in the signal were correlated to the ultrasound bursts). Also, the relatively small size of the tumors made experiments sensitive to the probe positioning with respect to the surface vessels and the position of the ultrasound; operator skill was a critical factor in experiment success.

In summary, the current study demonstrated that there are substantial and predictable ultrasound-induced changes in the $I_{560}/I_{540}$ ratio signal obtained through in vivo spectroscopic measurements of diffuse light reflected from tumor and nontumor mouse tissue. The ratio signal is better correlated to the ultrasound signal for nontumor tissue than tumor tissue and appears highly promising for noninvasive tissue diagnostics.

Two specific experiments will be described.

Figure 6A:
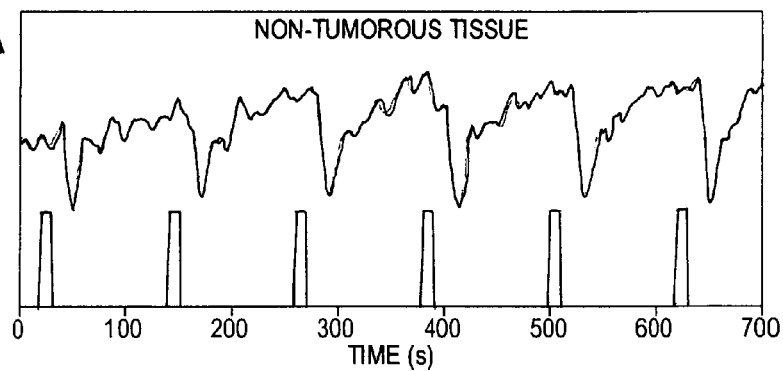
FIG. 6A shows the relationship between the ultrasound signal and dips in the $I_{560}/I_{540}$ signal in non-tumorous tissue.
Figure 6B:
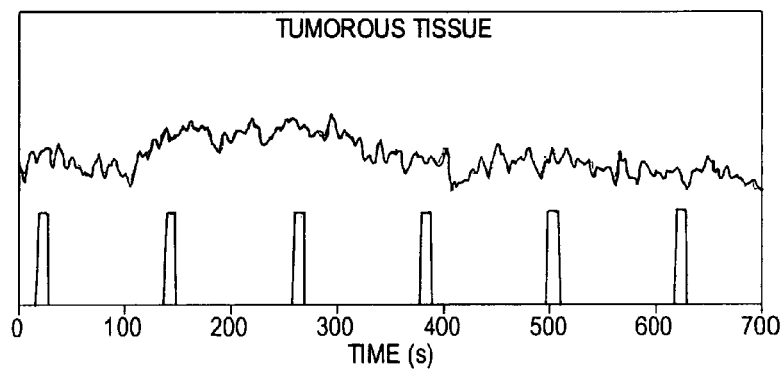
FIG. 6B shows the same in tumorous tissue.

By visual inspection of $I_{560}/I_{540}$ and its comparison with the ultrasound signal, one can establish a visual temporal correlation between the two in the non-tumor scans, and the absence of such a correlation in the tumor scans. As shown in FIGS. 6A and 6B, the ultrasound signal in non-tumorous tissue causes more prominent dips in the observed $I_{560}/I_{540}$ signal than in the tumorous tissue. The measurements were not always so obvious. Our first experiment was designed to demonstrate that it was possible to establish the mathematical correlation between the $I_{560}/I_{540}$ ratio and the ultrasound signal. The second experiment was aimed at the creation of a novel diagnostic algorithm based on a single experimental observation.

Figure 7:
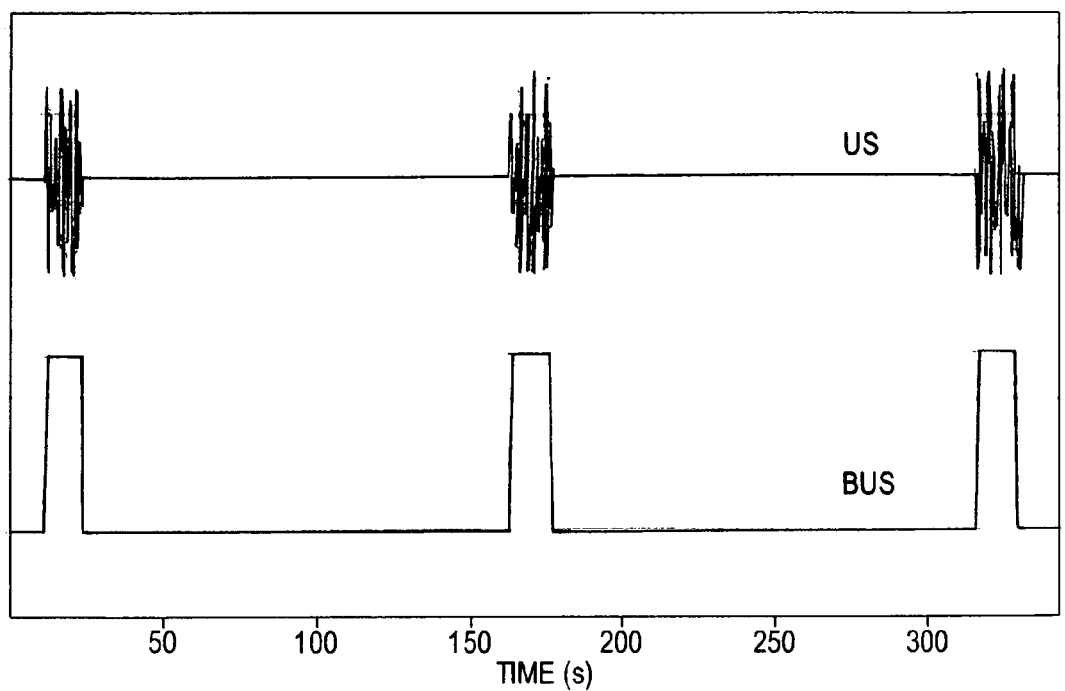
FIG. 7 shows the original ultrasound signal and its "boxed" representation.

In the first experiment, visual correlation between the $I_{560}/I_{540}$ ratio and ultrasound bursts was visually evident in most cases. The bursts of ultrasound caused pronounced drops in the observed $I_{560}/I_{540}$ signals. In this experiment, we quantified that correlation and demonstrated that it is significantly different between probe readings of tumor and non-tumor tissue responses. The algorithm we used in this experiment was as follows:

1. The original ultrasound (US) signal was modified ("boxed") (FIG. 7) as:

$$BUS = \begin{cases} 0 & .US \text{ off} \\ 1 & .US \text{ on} \end{cases} \quad (1)$$

2. The general slope (i.e. trend) of the $I_{560}/I_{540}$ signal was approximated using $2^{nd}$-degree polynomial interpolation, and the BUS (I) has been scaled down and adjusted to the signal trend:

$$AUS = \text{trend} - BUS/20 \quad (2)$$

3. To characterize the $I_{560}/I_{540}$ vs. US correlation, we used cross-covariance of $I_{560}/I_{540}$ and AUS. In statistics, cross-covariance assesses the degree to which two variables co-vary or vary together. It is computed as the mean of the products of the mean deviations for each variable in the observed set. Thus, the cross-covariance between recorded $I_{560}/I_{540}$ signal (R) and adjusted (AUS) ultrasound signal was calculated as cross-correlation function of two sequences with their means removed:

$$X\text{Cov}(m) = E[R(n+m) - MA^* \text{conj}(AUS(n) - MAUS)] \quad (3)$$

where MR and MAUS stand for the means of R and AUS respectively, E stands for the Mathematical Expectation, conj is the complex-conjugate operator, and m and n are position indices in the signal.

4. The XCov signal was smoothed using the Savitzky-Golay (polynomial) FIR smoothing filter, with the polynomial order 3 and window size 41.

5. The standard deviation of the smoothed XCov signal was calculated.

6. Standard deviations were calculated for measurements taken on both tumor and non-tumor hind legs, and the ratio of the measurements $$\mathrm{Std}(X\mathrm{Cov}_{nontumor})/\mathrm{Std}(X\mathrm{Cov}_{tumor}) \quad (4)$$

was calculated and recorded.

7. The procedures described in steps 1-6 were repeated for a total of 24 mice.

Figure 8:
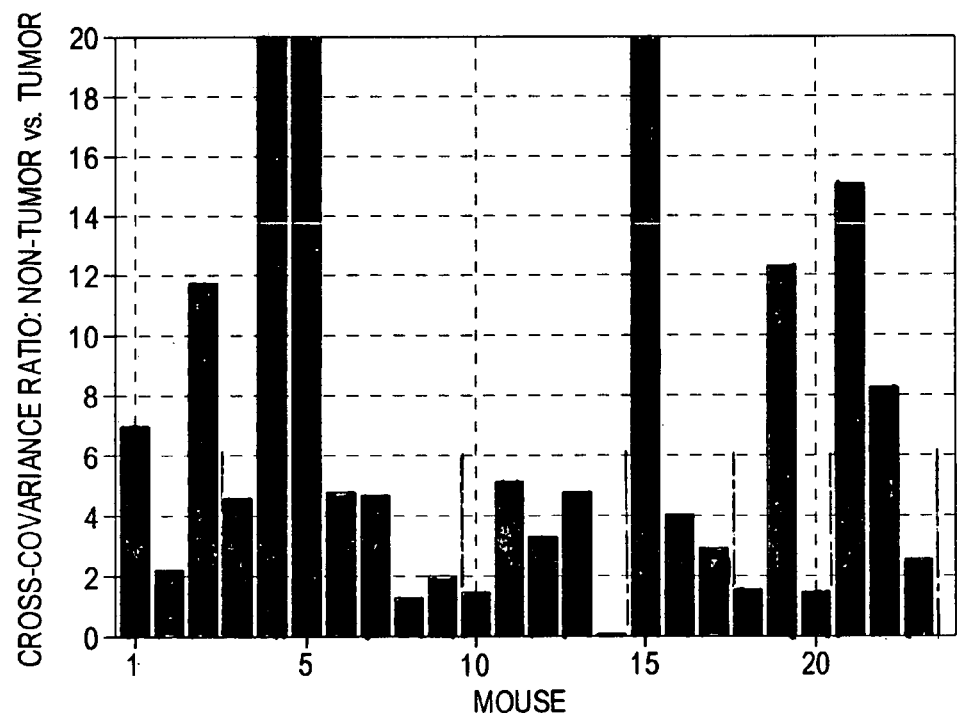
FIG. 8 shows a cross-covariance ratio for non-tumor vs. tumor.

Results of this experiment are presented in FIG. 8. The ratio of the standard deviations (4) was greater than 1 (one) in all but one experiment, and greater than 2 (two) in 75% of measured mice. The $I_{560}/I_{540}$ signal in non-tumorous tissue is better correlated to the ultrasound than the same signal for tumorous tissue, measured for the same mouse to compensate for physiological differences in mice population.

For the second experiment, upon confirmation that there was a correlation between ultrasound bursts and observed changes ("dips") in the observed signal, we constructed a novel diagnostic algorithm that utilized that information.

1. The ultrasound (US) signal was modified as in (1).

Figure 9:
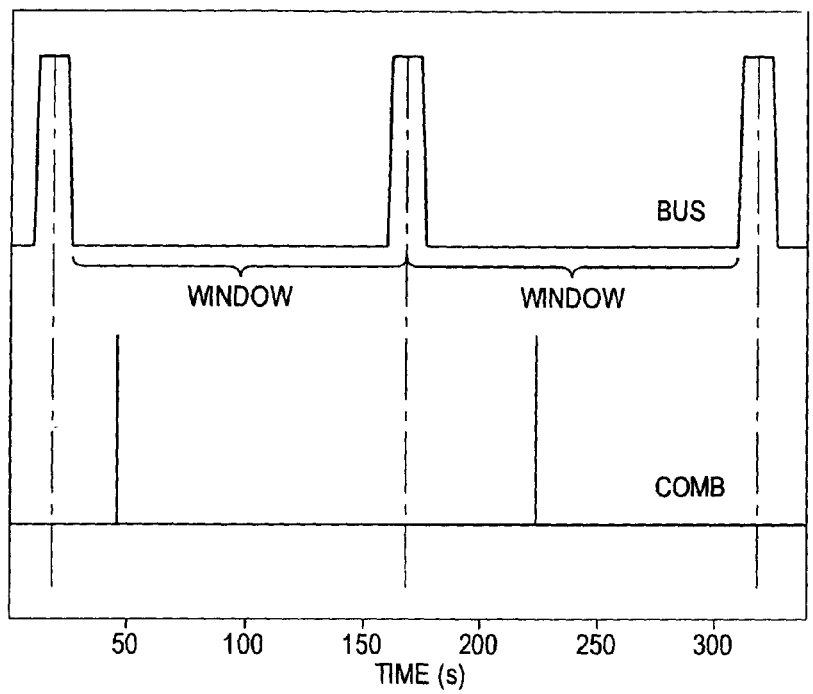
FIG. 9 shows a boxed ultrasound signal, the observation windows, and a comb signal with spikes at the positions of local minima.

2. Locations of the centers of each ultrasound burst were found and used to split $I_{560}/I_{540}$ to non-overlapping "windows" bounded by those centers. The end of observation at the right side bounded the rightmost "window." FIG. 9 shows a "boxed" ultrasound signal (BUS), observation "windows", and a comb signal (to be described below) with spikes at the positions of local minima (calculated for each "window").

3. The general slope (i.e. trend) of the $I_{560}/I_{540}$ signal was approximated using $2^{nd}$-degree polynomial interpolation, and the difference between trend and $I_{560}/I_{540}$ was calculated.

4. The positions of the local minima of the difference function (calculated for each "window") were calculated.

5. The new (comb) signal with ones at the position of local minimums, and zeros elsewhere was constructed (FIG. 9).

6. The maximum of the correlation between ultrasound (BUS) signal and comb signal was calculated.

7. The ratio $$r = (\mathrm{sum}(\mathrm{comb}) - \mathrm{max}(\mathrm{corr}))/\mathrm{sum}(\mathrm{comb}) \quad (5)$$

was calculated and compared to a decision threshold dt.

The experiment was repeated for varying values of the decision threshold, and a Receiver-Operating Characteristics (ROC) curve was calculated. The algorithm achieved the best results with the decision threshold set to dt=0.40: specificity was 83.3%, and sensitivity was 79.2%. Complete results of this experiment are presented in Table I and FIG. 10, which shows the ROC curve for the diagnostic algorithm. The decision threshold varied from 0.1 to 1 in 0.05 steps. The area under the curve is 0.90.

Figure 11:
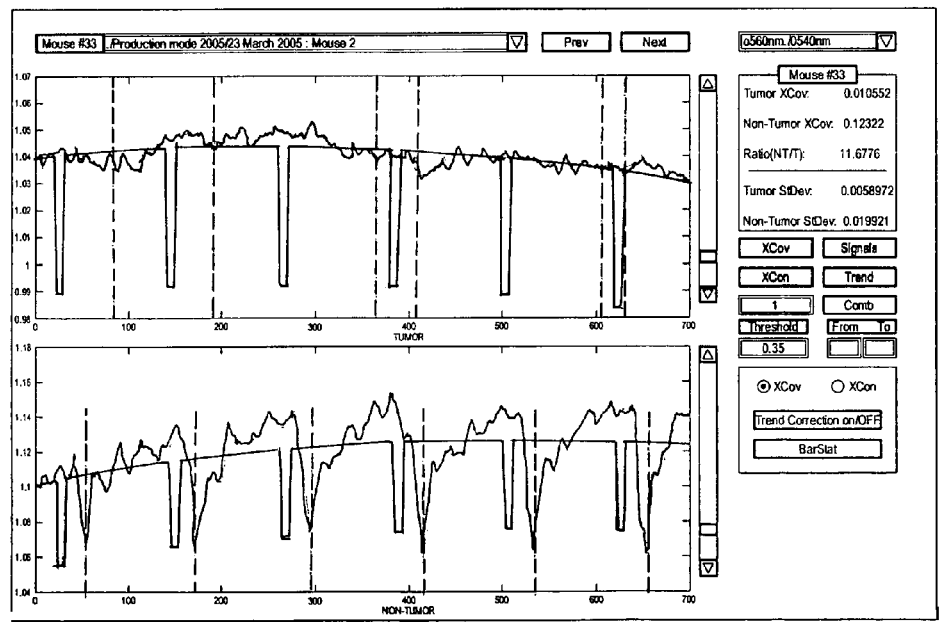
FIG. 11 shows a screen shot of the experimental tested with a trend adjusted ultrasound superimposed over the $I_{560}/I_{540}$ signal.

The experiment tested is presented in FIG. 11. In the screen shot of FIG. 11, trend adjusted ultrasound (AUS) is superimposed over the $I_{560}/I_{540}$ signal. Dashed lines denote positions of local minima.

TABLE I

EXPERIMENTAL DATA USED TO CALCULATE ROC

| Threshold | tp | fn | tn | Tp | Sensitivity | Specificity | PPV | NPV |
|---|---|---|---|---|---|---|---|---|
| 0.00 | 1.00 | 0.00 | 0.29 | 0.71 | 1.00 | 0.29 | 0.59 | 1.00 |
| 0.05 | 1.00 | 0.00 | 0.29 | 0.71 | 1.00 | 0.29 | 0.59 | 1.00 |
| 0.10 | 1.00 | 0.00 | 0.29 | 0.71 | 1.00 | 0.29 | 0.59 | 1.00 |
| 0.15 | 1.00 | 0.00 | 0.29 | 0.71 | 1.00 | 0.29 | 0.59 | 1.00 |
| 0.20 | 0.92 | 0.08 | 0.58 | 0.42 | 0.92 | 0.58 | 0.69 | 0.88 |
| 0.25 | 0.92 | 0.08 | 0.58 | 0.42 | 0.92 | 0.58 | 0.69 | 0.88 |
| 0.30 | 0.92 | 0.08 | 0.58 | 0.42 | 0.92 | 0.58 | 0.69 | 0.88 |
| 0.35 | 0.83 | 0.17 | 0.75 | 0.25 | 0.83 | 0.75 | 0.77 | 0.82 |
| 0.40 | 0.79 | 0.21 | 0.83 | 0.17 | 0.79 | 0.83 | 0.83 | 0.80 |
| 0.45 | 0.79 | 0.21 | 0.83 | 0.17 | 0.79 | 0.83 | 0.83 | 0.80 |
| 0.50 | 0.58 | 0.42 | 1.00 | 0.00 | 0.58 | 1.00 | 1.00 | 0.71 |
| 0.55 | 0.58 | 0.42 | 1.00 | 0.00 | 0.58 | 1.00 | 1.00 | 0.71 |
| 0.60 | 0.54 | 0.46 | 1.00 | 0.00 | 0.54 | 1.00 | 1.00 | 0.69 |
| 0.65 | 0.54 | 0.46 | 1.00 | 0.00 | 0.54 | 1.00 | 1.00 | 0.69 |
| 0.70 | 0.04 | 0.96 | 1.00 | 0.00 | 0.04 | 1.00 | 1.00 | 0.51 |
| 0.75 | 0.04 | 0.96 | 1.00 | 0.00 | 0.04 | 1.00 | 1.00 | 0.51 |
| 0.80 | 0.00 | 1.00 | 1.00 | 0.00 | 0.00 | 1.00 | nd | 0.50 |
| 0.85 | 0.00 | 1.00 | 1.00 | 0.00 | 0.00 | 1.00 | nd | 0.50 |
| 0.90 | 0.00 | 1.00 | 1.00 | 0.00 | 0.00 | 1.00 | nd | 0.50 |
| 0.95 | 0.00 | 1.00 | 1.00 | 0.00 | 0.00 | 1.00 | nd | 0.50 |
| 1.00 | 0.00 | 1.00 | 1.00 | 0.00 | 0.00 | 1.00 | nd | 0.50 |

True positives (tp) are correctly identified tumors, and true negatives (tn) are correctly identified non-tumors Results of the first experiment revealed evident differences between tumor and non-tumor measurements and demonstrated that optical spectroscopy measurements of acoustically induced blood stasis could be used to differentiate between tumor and non-tumor tissues in vivo. Variations in the experimental results (from mouse to mouse) were most likely related to variations in the experimental conditions (mouse movements, probe pressure, probe positioning, etc.).

The second experiment demonstrated that it is possible to quantitatively differentiate tumor from non-tumor based on a single non-invasive measurement. In this experiment, we first established the experimental procedure (constructed the decision-making algorithm) and then varied the value of the decision threshold in search of an optimum (the point on the curve closest to the (0,1) coordinates). It was found that for the decision threshold values of 0.40 and 0.45, the algorithm reached a specificity of 0.83 and a sensitivity of 0.79. As a measure of the algorithm accuracy, the initial assessment of the area under the ROC curve (by this experiment) was 0.90 (meaning that the constructed algorithm is indeed a very good classifier).

It is not necessary to apply principal component analysis (PCA) to construct the diagnostic discriminator. The reason is that the observed phenomenon of ultrasound contrast on blood vessels in normal tissue is much more pronounced than originally inferred from the literature. The simpler cross-covariance between the ultrasound pulse signal and the ratio of NIR signals at 560 vs. 540 nm ($I_{560}/I_{540}$) is sufficient to discriminate between malignant and normal tissue.

An intriguing finding throughout the experimental study is that the acoustic effect on blood vessels and tissue hemoglobin concentrations are very pronounced in the normal (non-tumor) leg, and almost completely absent in the tumor leg of the same mouse, except when the NIR probe was placed directly above a major blood vessel on the tumor side. Immunohistochemistry analysis performed on the tumor and non-tumor frozen sections approximately through the plane of the corresponding NIR measurement intersecting the ultrasound standing wave showed that the non-tumor side consisted of a regular network of blood vessels with spacing and directional regularity, whereas the tumor side consisted of a more sporadic network of vessel spacing and directionality. FIGS. 12A-12D show the result of that analysis. FIG. 12A shows the CD31 staining for the tumor (all vessels). FIG. 12B shows the corresponding DiOC$_7$ perfusion stain (perfused vessels). FIG. 12C shows the CD31 staining for contralateral normal tissue. FIG. 12D shows the corresponding DiOC$_7$. All images are at the same magnification.

The experimental finding that the sono-contrast is much more pronounced in non-tumor than tumor tissue indicates that the effect on blood flow and stasis by acoustic pressure is primarily a phenomenon of normal vessel network morphology and not malignant, angiogenic growth. We have constructed a theoretical hemodynamic model to fit the observed data for each animal. The sono-contrast NIR technique achieves diagnostic power through detection of vessel regularity and temporal hemoglobin content change. The existence of sporadic angiogenic network and/or vessel leakiness drastically reduces the expected sono-contrast. In the case of irregular, angiogenic growth, an acoustic standing wave will not cause the expected temporary stasis.

Figure 10:
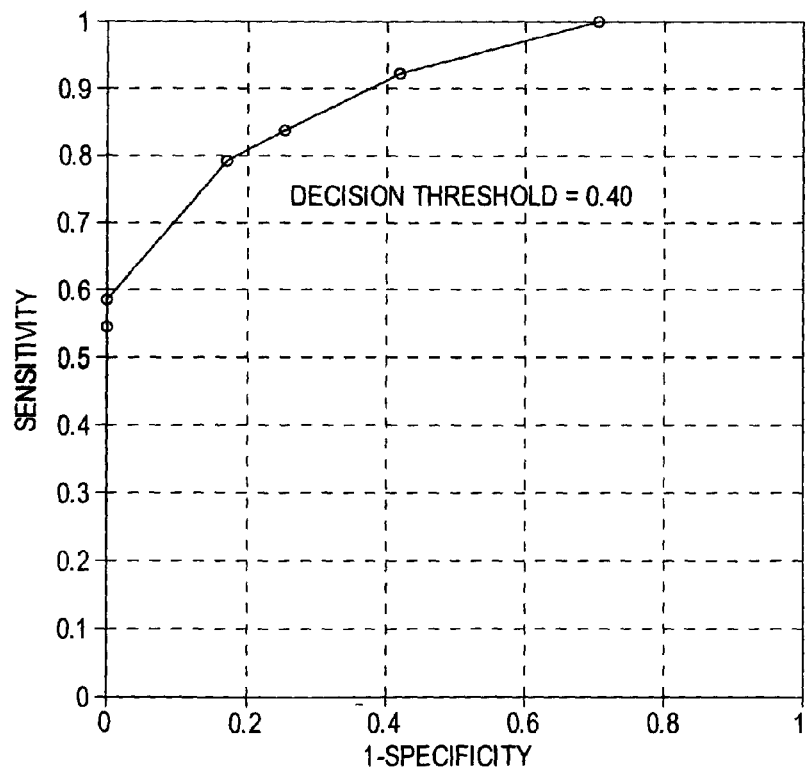
FIG. 10 shows an ROC curve for the diagnostic algorithm.

The above-mentioned difference in sono-contrast response between tumor and non-tumor was used as a diagnostic discriminator in the cross-covariance analysis of the $I_{560}/I_{540}$ ratio. To test the diagnostic power of the algorithm, a decision threshold was defined to demarcate the point between normal vs. malignant findings. When this decision threshold was varied and the algorithm re-run for the test population of 25 mice (50 data sets), an ROC curve was generated (FIG. 10). The area under the curve (AUC) was found to be 0.90. The standard deviation of the AUC was calculated using the standard bootstrap method, by randomly selecting sub-sets of 90% the test population with replacement. Averaged over 5 runs, the AUC was found to be 0.91±0.01.

One unforeseen difficulty originating from our proposed experimental method is that immunohistochemistry analysis could not be précised performed at the location containing the sono-contrast NIR measurement, This is because the latter is noninvasive, prior to animal sacrifice and freezing of the samples, whereas the former relies on slicing through a skin mark at an approximate orientation containing the noninvasive measurement. There is no one-to-one correspondence, therefore a linear correlation of the sono-contrast NIR data and immunohistochemistry data would not be a rigorous description of the relationship. Instead, we have chosen to perform regression analysis using each of a set of immunohistochemistry parameters as dependent variable, and a set of sono-contrast NIR parameters as independent variables. The complete sets of parameters are shown in Table II:

TABLE II

| | | Sono-Contrast NIR Parameters: |
|---|---|---|
| 1 | max_corr | Maximum of the cross correlation between the ratio signal and the US signal |
| 2 | max_cov | Maximum of the cross covariance between the ratio signal and the US signal |
| 3 | deci_val | Decision value for diagnosis |
| 4 | min_sig | Minimum of the ratio signal with baseline trend subtracted |
| 5 | std_sig | Standard deviation of the ratio signal with baseline trend subtracted |
| 6 | max_min_sig | Maximum minus minimum of the ratio signal with baseline trend subtracted |
| 7 | trend_diff | Difference between the endpoint values of the baseline trend line |
| | | Immunohistochemistry Parameters: |
| 8 | tot_ves | Average distance between all vessels in analysis area |
| 9 | perf_ves | Average distance between perfused vessels in analysis area |
| 10 | perf_area | Percentage of perfused vessel area in analysis area |
| 11 | tot_area | Percentage of all vessel area in analysis area |
| 12 | mean_dist | Mean EF5 intensity for all vessels |
| 13 | Std_dist | Standard deviation of average distance for all vessels |
| 14 | skew_dist | Skew of EF5 intensity for all vessels |
| 15 | kurt_dist | Kurtosis of EF5 intensity for all vessels |
| 16 | mean_perf | Mean EF5 intensity for perfused vessels |
| 17 | skew_perf | Skew of EF5 intensity for perfused vessels |
| 18 | kurt_perf | Kurtosis of EF5 intensity for perfused vessels |

Results of the regression analysis are shown in Table III. It can be seen that there exist strong predictive relationships between three solo-contrast NIR measurement parameters, namely, (a) the magnitude of change in $I_{560}/I_{540}$, (b) the standard deviation of $I_{560}/I_{540}$, and (c) the baseline change before and after ultrasound pulse insonification, with certain immunohistochemistry parameters, namely, percent area of perfused vessels, total number of vessels, mean distance between vessels (both total and perfused), and standard deviation of the vessel distribution. Among these, (a) and (b) together are predictive of the total number of vessels at p<0.01.

TABLE III

| Dependent Variable | Statistically Significant (p < 0.05) Predictors from Regression Analysis | p value |
|---|---|---|
| Percentage of perfused vessel area in analysis area | Maximum minus minimum of the ratio signal with baseline trend subtracted | p = 0.031 |
| | Standard deviation of the ratio signal with baseline trend subtracted | p = 0.015 |
| Average distance between all vessels in | Maximum minus minimum of the ratio signal with baseline trend subtracted | p = 0.008 |

TABLE III-continued

| Dependent Variable | Statistically Significant (p < 0.05) Predictors from Regression Analysis | p value |
| --- | --- | --- |
| analysis area | Standard deviation of the ratio signal with baseline trend subtracted | p = 0.005 |
| Mean EF5 intensity for all vessels | Difference between the endpoint values of the baseline trend line | p = 0.013 |
| Mean EF5 intensity for perfused vessels | Difference between the endpoint values of the baseline trend line | p = 0.012 |
| Standard deviation of average distance for all vessels | Maximum minus minimum of the ratio signal with baseline trend subtracted | p = 0.023 |
|  | Standard deviation of the ratio signal with baseline trend subtracted | p = 0.014 |

This part of the analysis clearly demonstrates that the magnitude of sono-contrast in the NIR spectrum and its variability are strongly predictive of vascular morphology and tissue perfusion.

Another intriguing observation not discussed in our reports is that some tissues respond to periodic. repeat insonification by a baseline gradual increase of $I_{560}/I_{540}$, which is an indicator of tissue oxygenation, whereas other tissues do not show this response (e.g., compare FIG. 2A with FIG. 5). The baseline change or non-change (labeled as trend_diff in Table II) is irrespective of tumor or normal tissue.

Clinical systems based on the above findings will now be disclosed.

Figure 13:
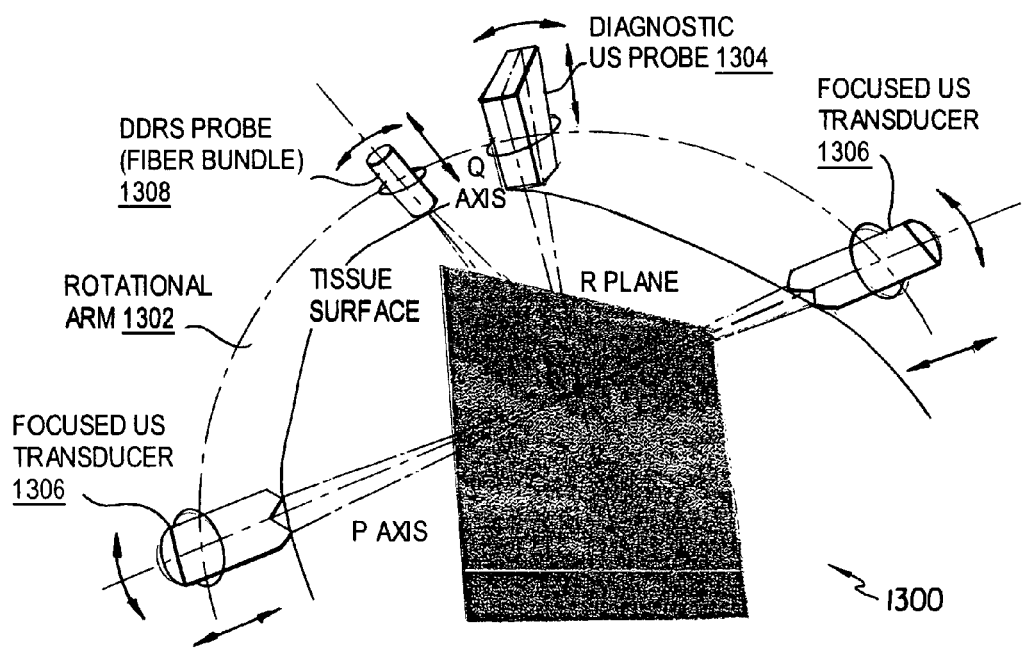
FIG. 13 shows a clinical system for breast cancer diagnosis.

FIG. 13 shows a clinical system 1300 for breast cancer diagnosis. The system is mounted on a track 1302 that can rotate around the breast, giving it the ability to inspect any region of the breast. The diagnostic ultrasound probe 1304 will be used to determine the region on which the physician will focus attention using the clinical system. The focused ultrasound probe 1306, DRS probe 1308, and diagnostic ultrasound probe 1304 are independently movable radially along the rotational arm as well as depth-wise along each mounting bracket attached to the arc.

Figure 14:
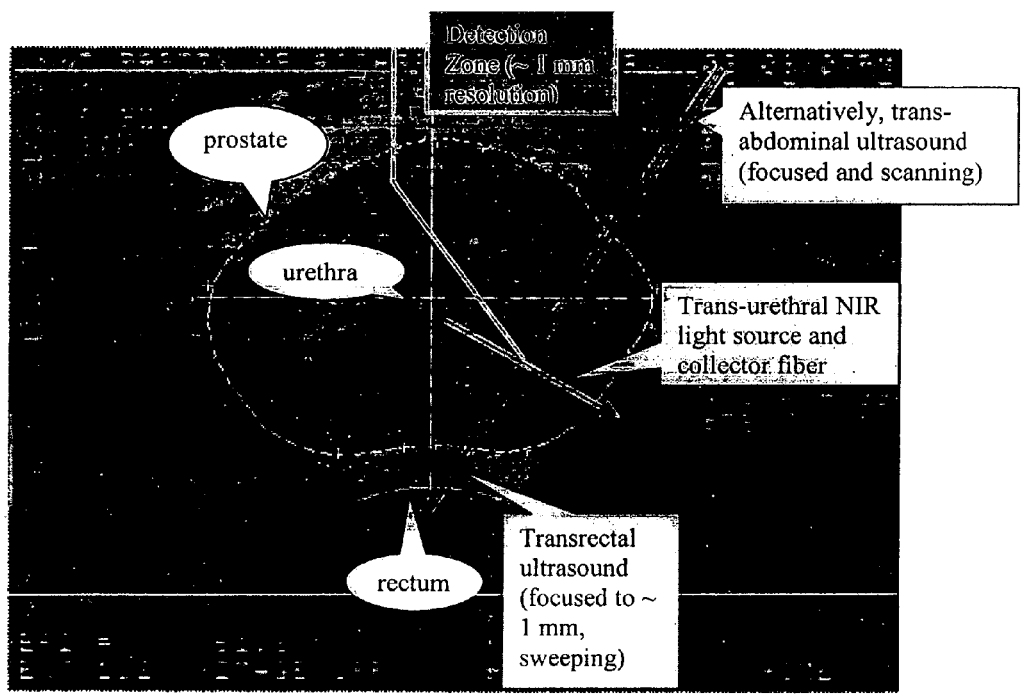
FIGS. 14 and 15A-15C show an embodiment for use with the prostate

FIG. 14 shows a screen shot of the use of an embodiment of the present invention with the prostate. In this figure, two alternative methods of applying focused ultrasound are illustrated: (1) trans-rectal; (2) trans-abdominal. In either case, infrared light source and collection fibers are applied via a trans-urethral catheter design. By sweeping the ultrasound path and the IR light source path, a high-resolution volume of the prostate may be interrogated in vivo for cancer characteristics.

Figure 15A:
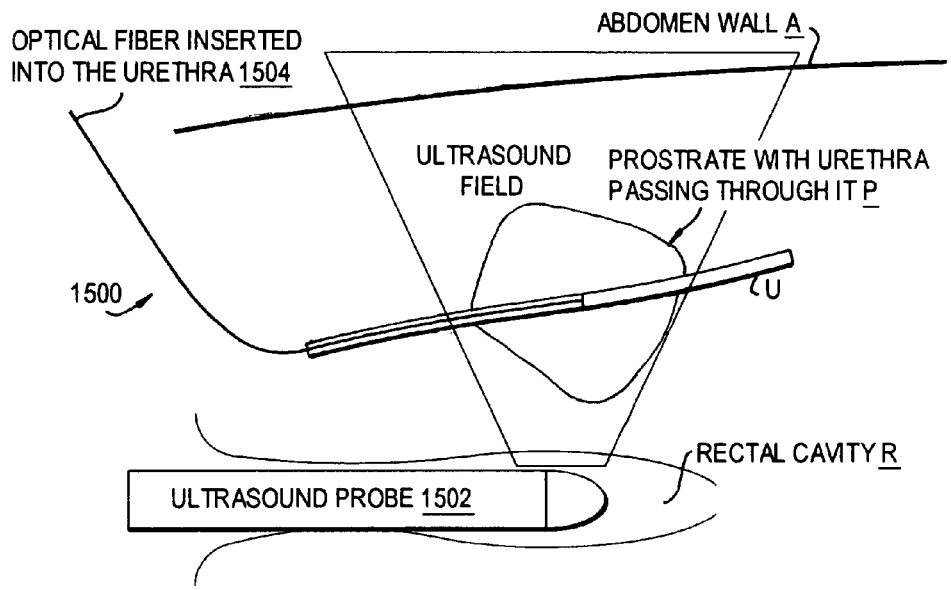
Figure 15B:
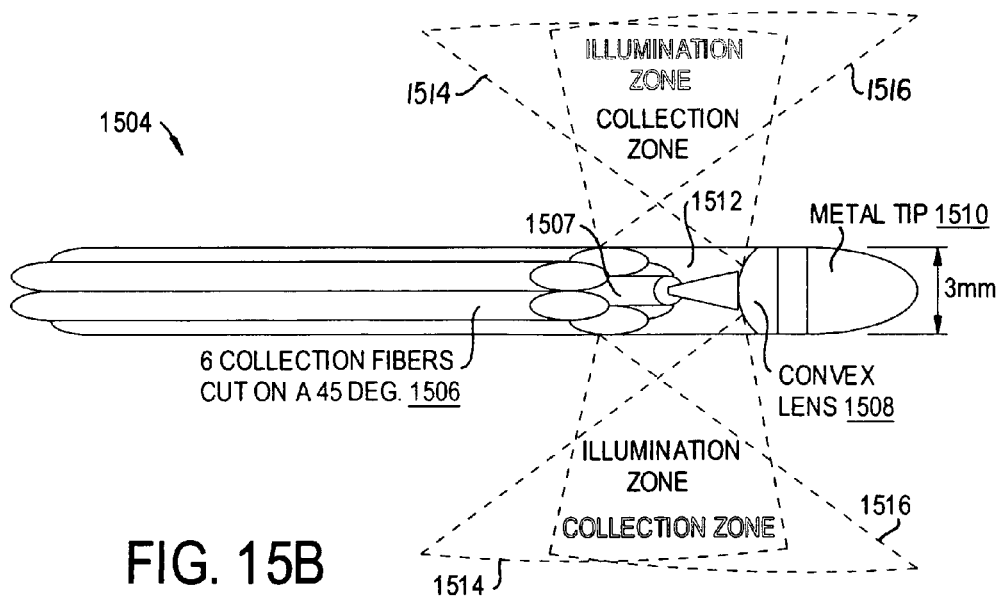
Figure 15C:
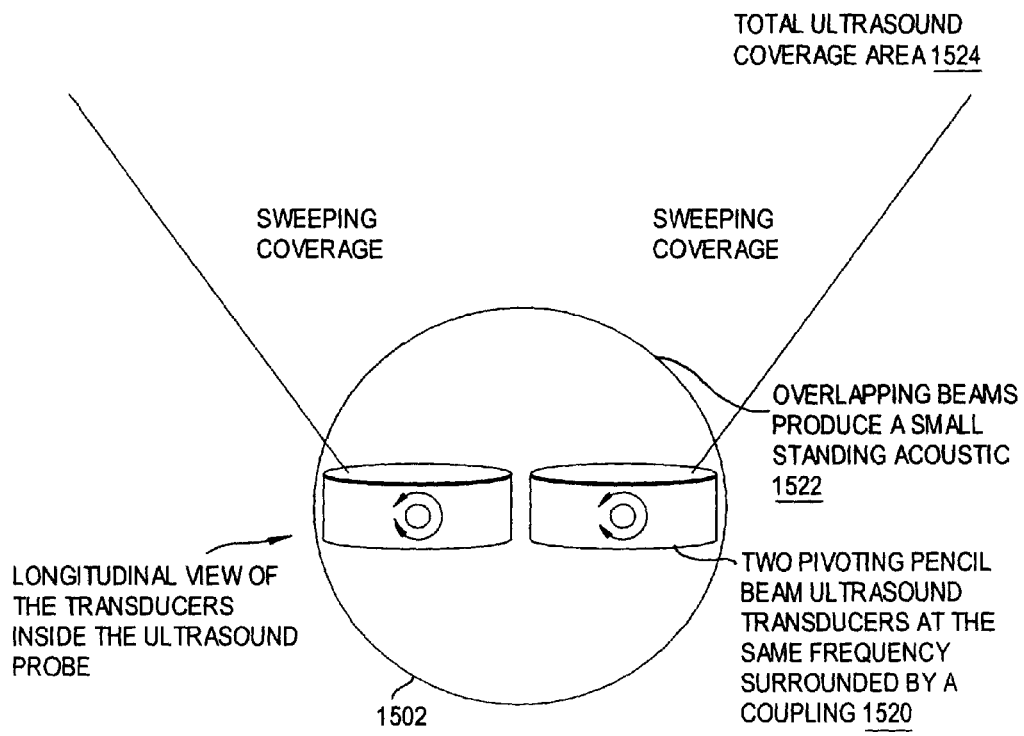

A side view of the prostate embodiment in use is shown in FIG. 15A. FIG. 15B shows the fiber design, and FIG. 15C shows the ultrasound probe. As shown in FIG. 15A, the system 1500 comprises an ultrasound probe 1502 and an optical fiber spectroscopy probe 1504. the ultrasound probe is inserted into the patient's rectal cavity R to emit ultrasound through the prostate P to the abdominal wall A. The optical fiber probe 1504 is inserted into the urethra U.

As shown in FIG. 15B, the optical spectroscopy probe 1504 includes six collection fibers 1506 cut on a 45° inclination, surrounding an illumination fiber 1507. The probe has a metal tip 1510 and a convex lens 1508 to define optical paths between the fibers 1506 and the outside through a transparent, soft tip 1512, thereby defining illumination zones 1514 and collection zones 1516.

The optical spectroscopy probe is inserted through the urethra until the transparent, soft tip is located at the center of the prostate. The optical probe continuously samples the entire volume of the prostate using a single illumination fiber located at the center of six collection fibers. After exiting the source fiber, the light will be diffused into the tissue after reflection off of a convex lens. The collection fibers will be cut at a 45° angle to allow for the sampling of light passing through the transparent sides of the optical probe. All six of these fibers will be attached to a TE cooled spectrometer, and samples will be collected at 50 ms intervals (20 Hz).

The dual transducer ultrasound probe 1502 is inserted into the rectal cavity. As shown in FIG. 15C, the ultrasound probe 1502 includes dual pencil beam transducers 1520 produce a stationary acoustic wave only in the region of overlap 1522. The transducers will create beams with diameters of 1 cm, creating a volume of overlap of ≈3 cm$^3$. This overlap volume can be swept over the entire volume of the prostate by rotating the transducers independently to provide a total ultrasound coverage area 1524; this will create the localized acoustic contrast for image construction.

Another area to which the present invention can be applied is localized drug delivery. The standing wave ultrasound causes reversible blood stasis in a localized area. The present invention can be used to arrest the blood flow with drugs present and to expose them to an optical stimulation signal. The effects of the drug can be minimized to the area of blood flow stasis. This can also be accomplished with normal, non-photosensitive drugs.

The three above-mentioned variations will now be disclosed.

In the first variation, two ultrasonic transducers are driven by an external amplifier capable of therapeutic power delivery, with the ultrasonic beams intersecting at an angle such as 90 degrees, which in turn defines the region of HIFU. This region is first visualized by such means as a diagnostic ultrasound probe positioned through the central axis, and its tissue characteristics may be interrogated via optical spectroscopy. A well circumscribed mass can be ablated in the breast or another suitable part of the body. Those skilled in the art who have reviewed the present disclosure will readily appreciate that any of the systems disclosed herein, or any other suitable system, can be used to implement the first variation.

Using the present invention, it is possible to re-oxygenate the tumor volume prior to, during or immediately after a period of radiation delivery, via such mechanisms as reactive hyperemia from focused ultrasound, as demonstrated in our previous disclosure. For example, focused ultrasound can be directed at the tumor cavity when the patient is positioned for treatment of breast cancer using modern, computer-controlled linear accelerator. After a pre-determined dose is delivered, the radiation is switched off, and the ultrasound pulse is activated briefly to manipulate blood flow in the region in a fashion to accelerate re-oxygenation, thus shortening the requirement for fractionation from one fraction per day to approximately 50 sec. per fraction. This is the principle on which a new era of radiation treatment of cancers via rapid fractionation is based. Those skilled in the art who have reviewed the present disclosure will readily appreciate that any of the systems disclosed herein, or any other suitable system, can be used to implement the second variation.

For the third variation, the inventors have designed a scanhead capable of delivering focused acoustic stationary fields up to 4 cm deep in the tissue. The two 1 MHz focused transducers are aligned in a single plane at 90 degrees. The focal zone is approximately 1 cm in diameter and, with a 5 second exposure, can be shown to successfully stop blood flow. The field intensity is within the FDA diagnostic limit and generates less than 1 C local temperature increase.

The scanhead also incorporated a fiber array (see FIG. 4 for an example array). The fiber array is connected to a dual wavelength diode light source (680 and 830 nm; other wavelengths are also possible) which is split into 9 fibers placed on the surface of the tissue with the scanhead. The collection fibers are combined into a single fiber which terminates at a room temperature spectroscope. The collection fibers can be separated and the sources intensity modulated for diffuse optical imaging.

The final component of the scanhead is a commercial ultrasound probe. The ultrasound probe is located in the same plane as the focused transducers and is used for image coregistration with the near infrared spectroscopy information, tissue density information and blood flow information.

The scanhead is designed to be gently placed upon the surface of the skin, above the tumor or questionable tissue. This information is gathered with a pre-scan ultrasound or mammogram. After the scanhead is placed on the surface of the skin, the optical data collection is begun. From this point to the conclusion of the exam, the scanhead is not moved. Any motion of the tissue or the scanhead will destroy image correlation.

In order to minimize motion of the scanhead, the ultrasound probe and focused transducers are given two degrees of freedom (DOF) within the scanhead in order for the focal zone to be positioned at various depths and lateral locations with respect to the tumor. This will generate a two dimensional map of the tissue surrounding and including the questionable tissue sample.

To use this system for diagnosis, monitoring of disease, progression or remission, the following steps are envisioned:
1. Position scanhead on patient at convenient angle; fix all scanhead support joints.
2. Use diagnostic ultrasound probe to verify alignment of focal center; move assembly axially away from or near patient's skin if necessary, so as to aim at desired depth in vivo.
3. Acquire baseline optical information.
4. Switch on focal ultrasound; acquire optical information.
5. Switch off focal ultrasound; acquire optical information.
6. Repeat steps 4-5 if necessary, allowing adequate interval in between.
7. To scan laterally, move assembly to left or right by manual or motorized actuation.
8. To scan depth-wise, move assembly axially away from or near patient.
9. To construct 2D imaging representation of data, scan in both directions.
10. To construct 3D image volume, it is necessary to scan adjacent planes or radially (see FIG. 5).

Figure 16:
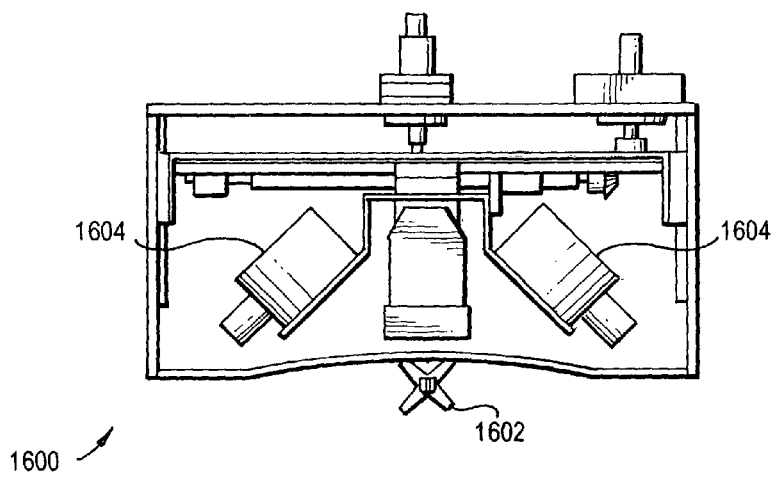
FIGS. 16, 17, 18A, 18B, 19 and 20 show an embodiment for use with the breast.
Figure 18A:
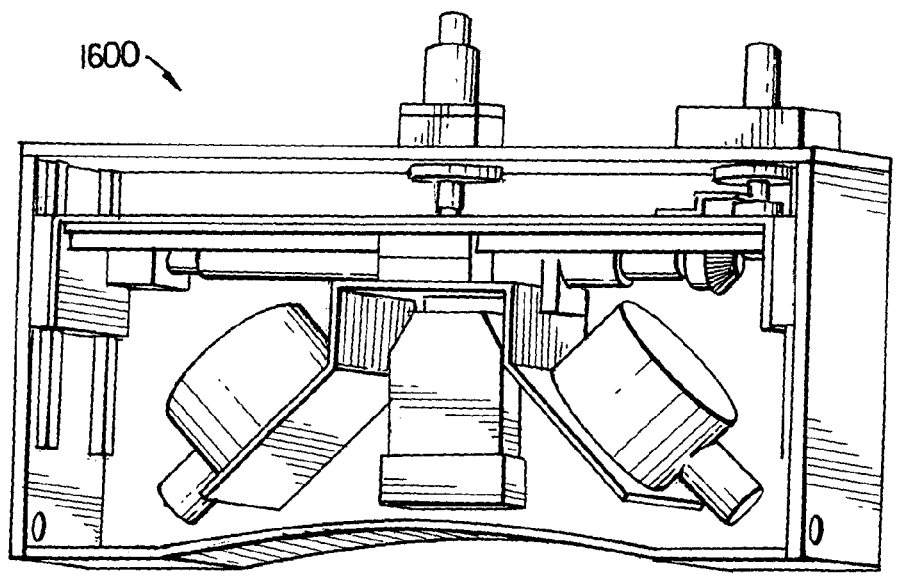
Figure 18B:
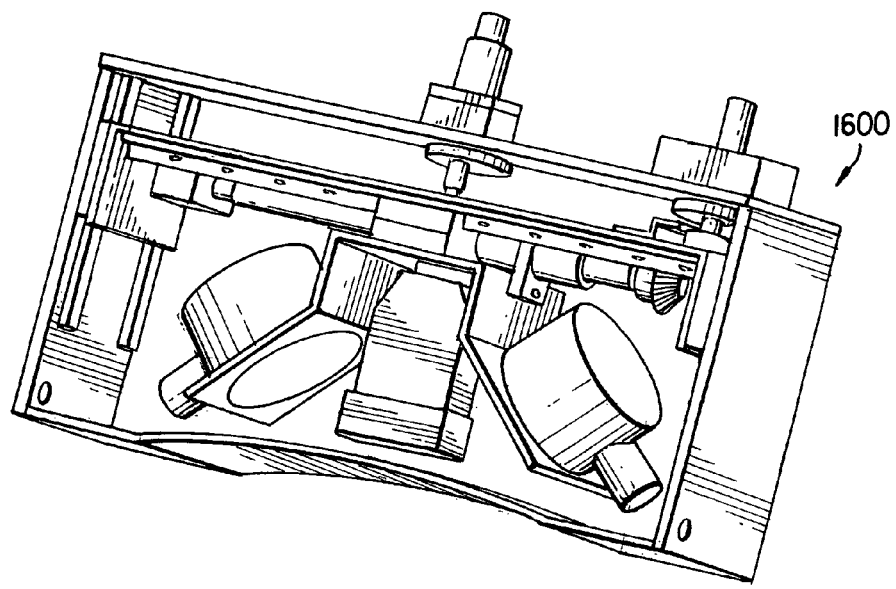

FIG. 16 shows the scanhead 1600 placed upon the surface of the skin. The cross 1602 is a simulated focal zone produced by the dual focused transducers 1604 aligned at 90 degrees. FIGS. 18A and 18B show three-dimensional views of the scanhead 1600.

Figure 17:
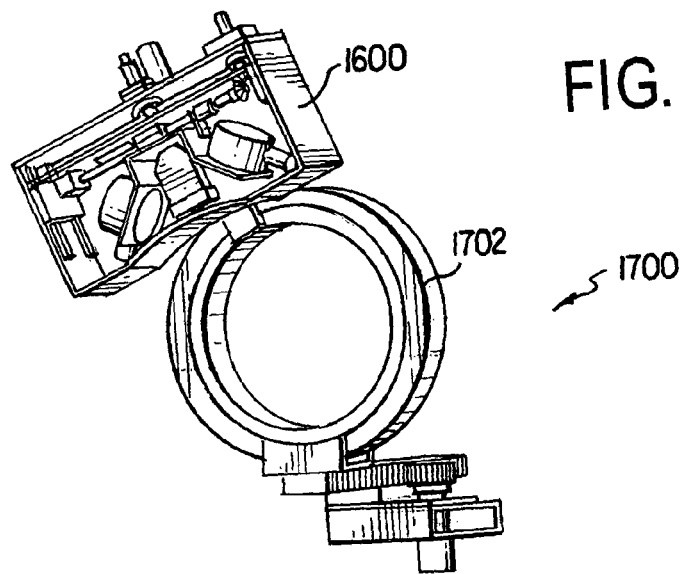

The delivery mechanism 1700 of FIG. 17 is capable of positioning the scanhead 1600 at any angle, depth and height. We employ a 360 degree ring assembly 1702 to rotate the scanhead 1600 around the breast. The delivery mechanism can translate the scanhead along a radial path to place the scanhead on the surface of the skin with only minor compression. Additionally, the mechanism can position the entire radial and angular elements along the lateral dimension of the breast.

Figure 19:
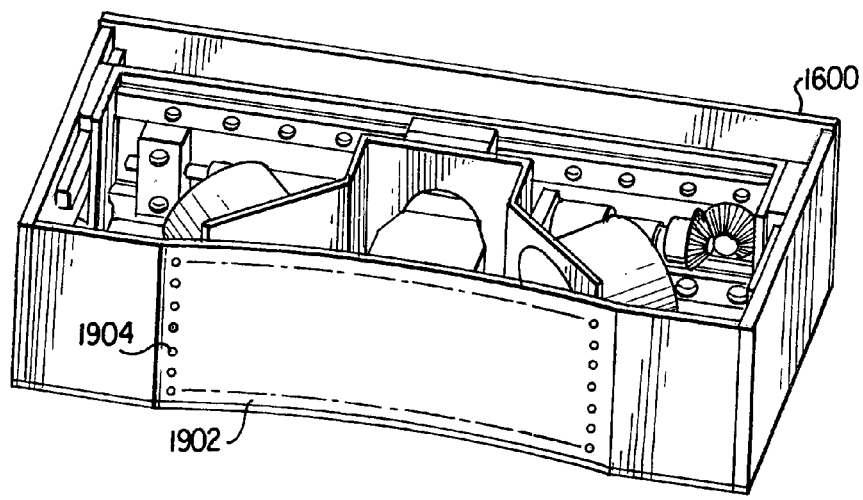

FIG. 19 shows a fiber array 1902 on a curved surface 1904 of the scanhead 1600. The curvature is designed to fit comfortably to the patient anatomy where the scan will take place.

Figure 20:
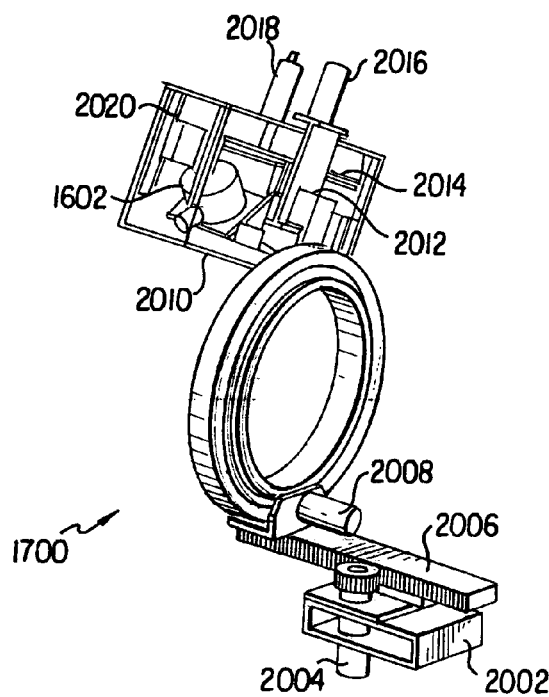

FIG. 20 shows an example of motorized mechanisms in the delivery mechanism 1700 for scanning and positioning the scanhead 1600 around the breast. In addition to the cross ring bearing 1702, shown a re a base 2002, a T1 DC motor and encoder 2004, a linear guide 2006 with gear rack, an R2 DC motor and encoder 2008, a T3 translation joint 2010, a T5 motor and encoder 2012, a linear guide T5 2014, a T3 motor and encoder 2016, a T4 motor and encoder 2018, and a linear guide T4 2020.

Figure 21A:
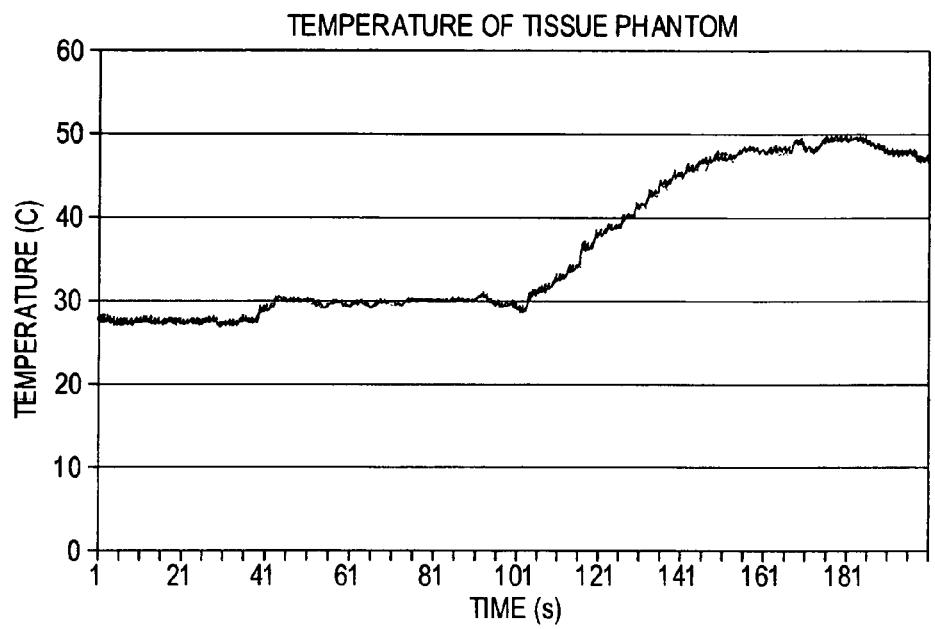
FIGS. 21A and 21B are plots showing experimental verification of the ablation embodiment.
Figure 21B:
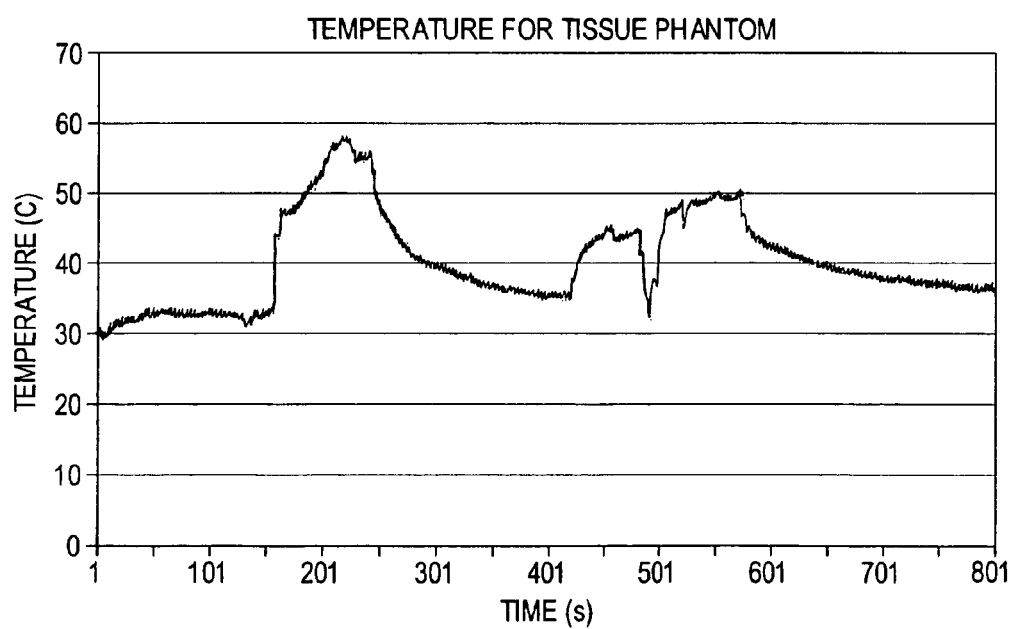

Experimental results from the ablation variation will now be described. Plots of those experimental results are given in FIGS. 21A and 21B. The current dual transducer model was tested using a soft PVC tissue phantom with similar acoustic properties to tissue and harvested turkey breast tissue sample. Both models exhibited extreme tissue heating in a localized region at the overlap of the focal zones of the two transducers. FIGS. 21A and 21B show the heating observed with a thermistor in the PVC tissue phantom when placed at the focal zone overlap during sonication from two transducers each driven by 12 W. FIG. 21B shows a temperature curve for two bursts (starting at 155$s$ and 420$s$) of ultrasound generated by two transducers in a PVC tissue phantom in a small (<2 mm$^3$) focal zone. The dip during the second pulse is due to a small vibration that displaced the thermistor sensor less than 1 mm from the focal zone overlap.

For both experiments, the amplifier was operated at full power, and the output was split between the two transducers. The input signal was 1.132 MHz. The two transducers were placed at approximated 90 deg. relative to each other, and the focal zones were overlapped.

For the test whose results are shown in FIG. 21A, the thermistor was moved close to the focal zone, and the temperature can be observed to increase.

For the test whose results are shown in FIG. 21B, the thermistor again was moved close to, probably into, the focal zone of the two transducers. The result is the first rise in temperature (maximum was 57.7° C.). The ultrasound was turned off, and the drop is quite sudden followed by an exponential decrease. When the temperature reached 35° C., the ultrasound was turned on again, resulting in the second temperature rise. The ultrasound was turned off and a similar exponential decrease was observed. There is a sharp dip in the second temperature rise which is probably due to vibration and displacement of the thermistor. Due to the small size and somewhat unknown location of the focal zone overlaps of the two transducers, the thermistor was difficult to place in the region.

Figure 22C:
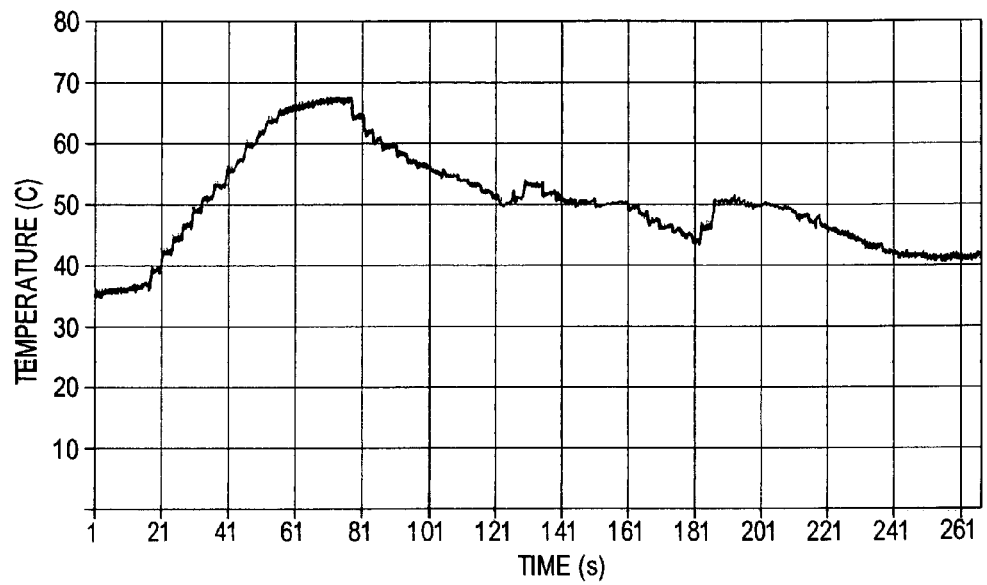
FIGS. 22A-22C are plots showing further experimental verification of the ablation embodiment, using a turkey breast.
Figure 22A:
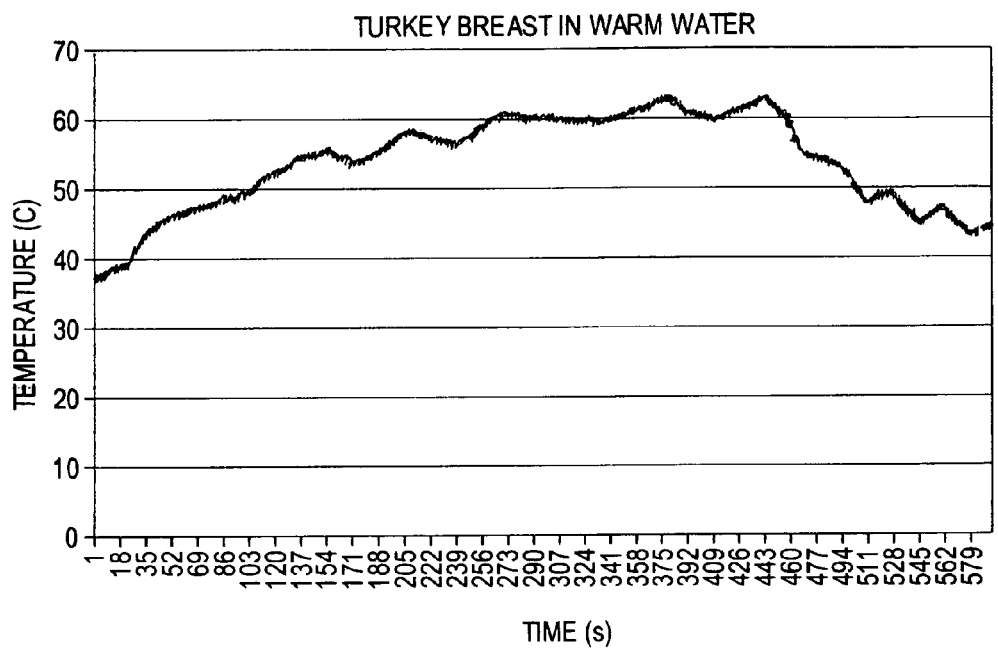

Additional experimental verification, using low input power, is given in FIGS. 22A-22C and 23A-23E. FIG. 22A shows a plot of temperature versus time in a sample, which is a turkey breast in water. For FIGS. 22B and 22C, the turkey breast samples were tested in two configurations: imbedded in the PVC tissue phantom (FIG. 22B) and submerged in a warm (37 C) water bath (FIG. 22C).

Figure 22B:
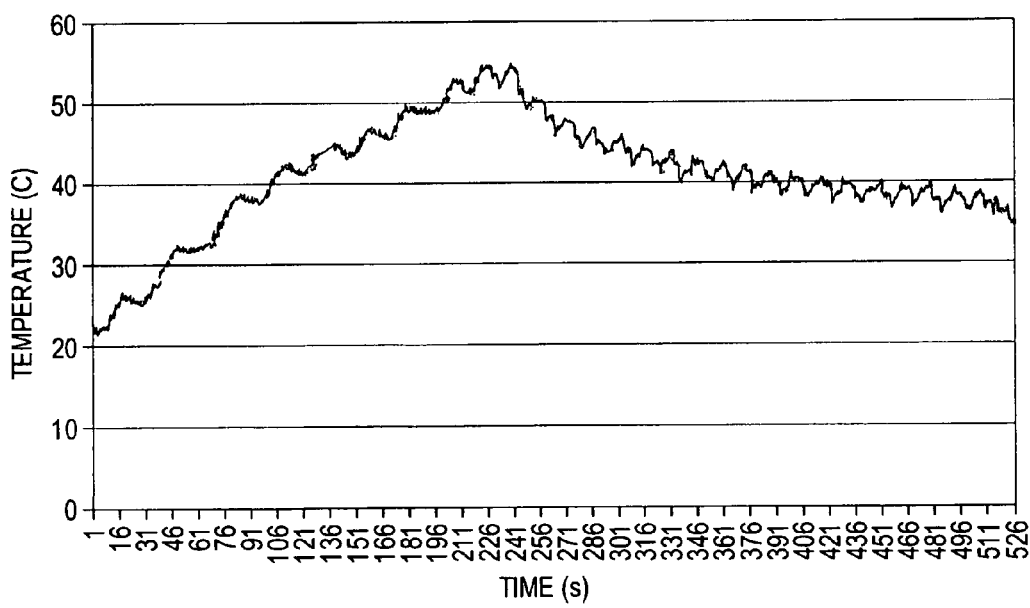

For the PVC imbedded samples, each transducer was driven at about 12 W, a reduction of between 2-30 times the intensity used in previous works. FIG. 22B shows the heating observed in the turkey breast sample imbedded in the PVC tissue phantom and exposed to a four minute burst of low power acoustic fields. The oscillations are due to thermal fluctuations with the environment.

In the water bath tests, a reflector acted as the second transducer and the driving power of the single transducer was about 22 W or 1.5-20 times less power than that used in previous studies. FIG. 22C shows the heating observed in the turkey breast sample submerged in the warm water bath. The ultrasound burst time length is one minute and the maximum temperature is 67 C. The transducer was driven by a 22 W signal with a reflector providing the second acoustic field.

Figure 23A:
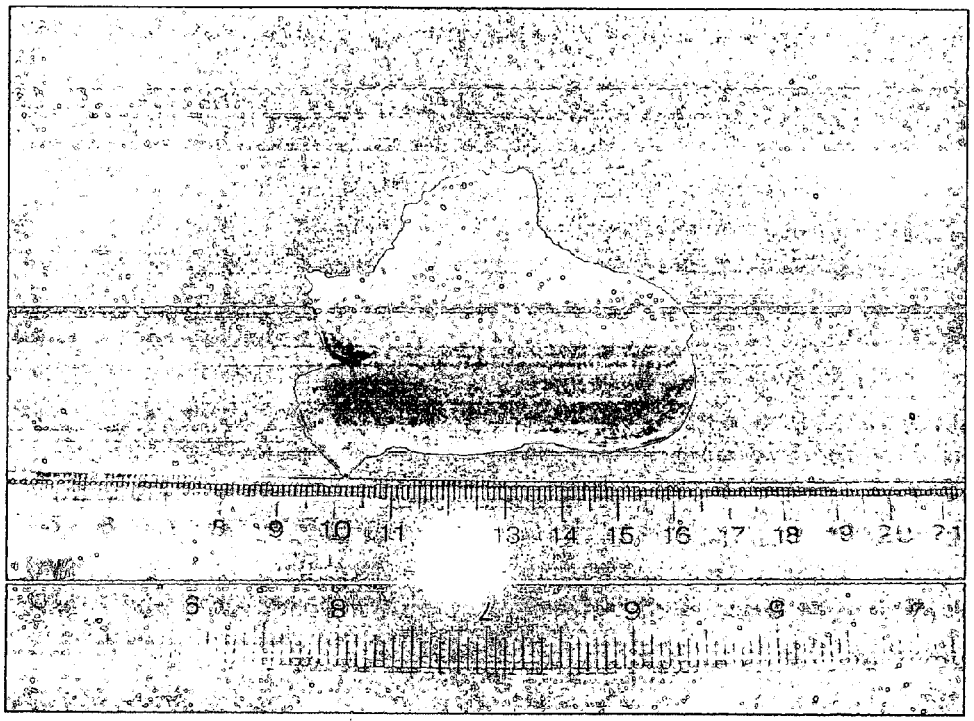
FIGS. 23A-23E are photographs showing the effect of the ablation on the turkey breast.
Figure 23B:
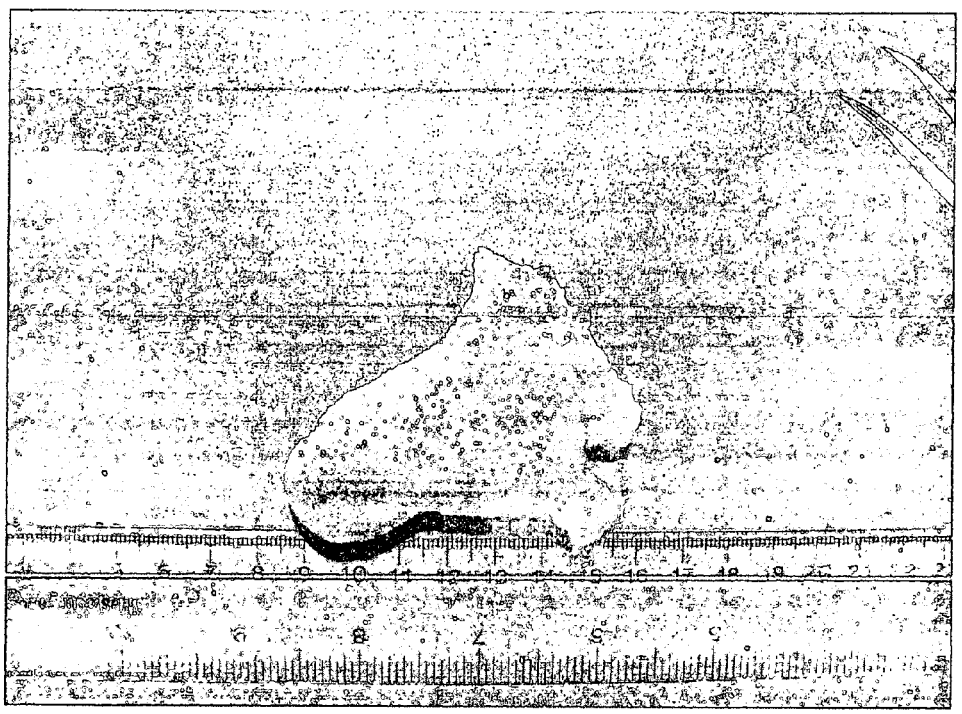
Figure 23C:
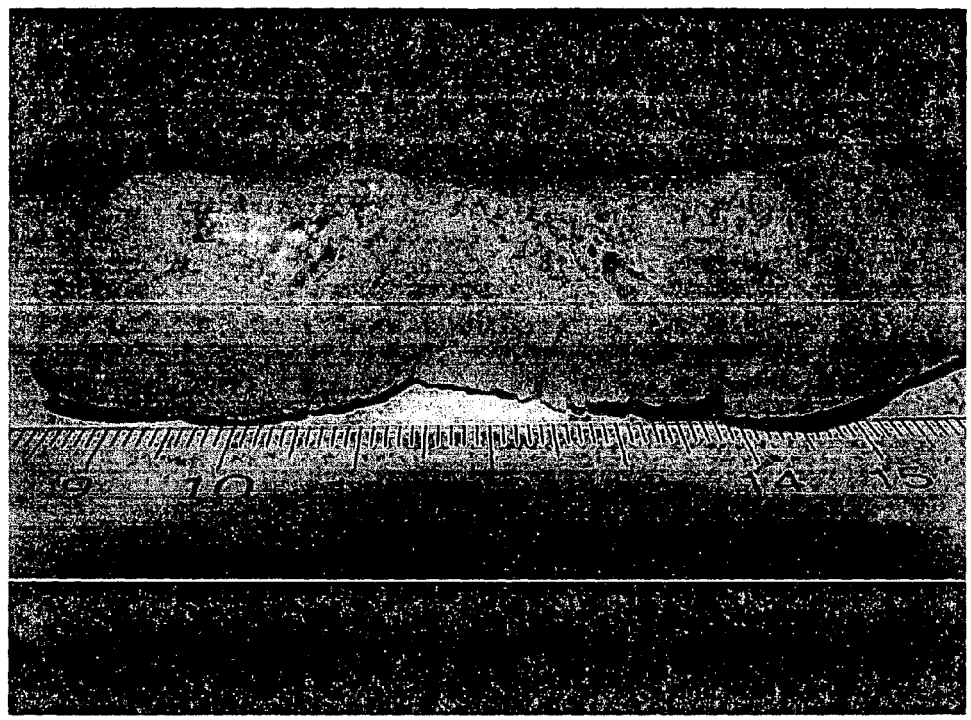
Figure 23D:
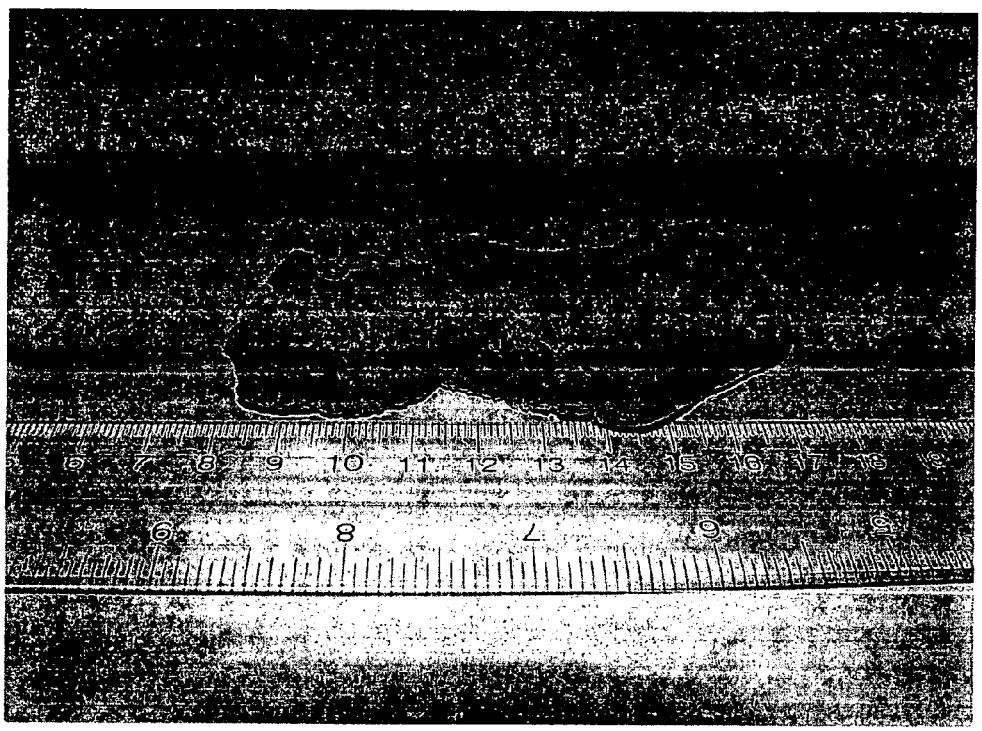
Figure 23E:
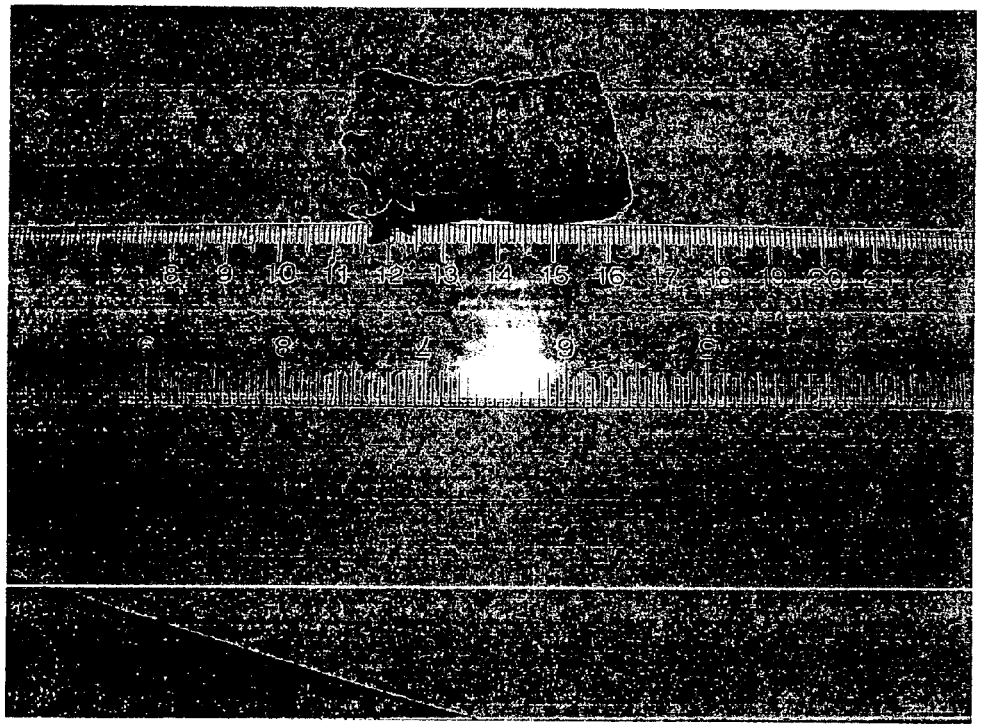

FIGS. 23A-23E show the turkey breast itself and make visible the effects of the ablation. The turkey breast samples were dissected following sonication for analysis of heating efficacy and volume analysis of the focal zone. For the dual transducers, the tissue samples exhibited "cooked" volumes in the range of 5 mm to 7 mm spherical diameters. The single transducer with reflector averaged "cooked" tissue ellipsoidal volumes of 5 mm by 15 mm, minor and major axes. FIG. 23C in particular demonstrates the white tissue that was cooked with the ultrasound in the single transducer setup.

Figure 24:
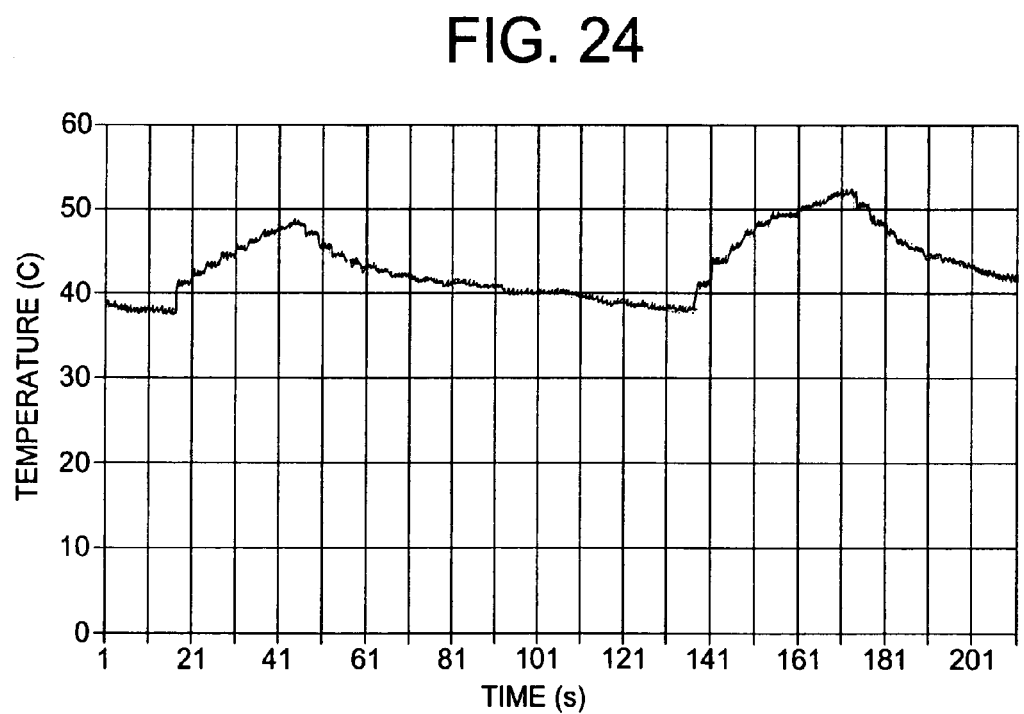
FIG. 24 is a plot showing the heating of the turkey breast sample by two ultrasound bursts, without a reflector and with a reflector.

As a comparison to a single transducer system, experiments were conducted on the submerged turkey breast sample with an aluminum reflector and without a reflector but with a rubber absorber. FIG. 24 demonstrates the difference in maximum attainable temperature for the two scenarios. The turkey breast tissue sample was heated by two ultrasound bursts: (1) without a reflector and (2) with a reflector in place. The maximum temperature difference is about 5 C The maximum temperature is not largely different but the total deposited heat energy and $t_{43}$ equivalent are significantly different. With a reflector (secondary acoustic source) the total deposited heat energy and $t_{43}$ equivalent were more than double those quantities achieved without a reflector in place. This outcome is due to the temperature rising much faster and the higher maximum temperature.

The present system has been demonstrated to heat both PVC tissue phantoms and turkey breast tissue sample to sustainable temperatures capable of tissue ablation. The dual transducer setup has been shown to generate a high intensity acoustic field and high temperatures in a very small volume using intensities much lower than previously published works. The lower intensities greatly reduce the risk of surface burning and tissue damage outside of the focal region. The dual transducer setup has been shown to produce a very small and geometrically predicable high intensity zone where temperatures rise up to 40 C from the ambient temperature but only in a small volume.

While a preferred embodiment has been set forth in detail, those skilled in the art who have reviewed the present disclosure will readily appreciate that other embodiments can be realized within the scope of the invention. For example, numerical values are illustrative rather than limiting, as are modalities of diagnosis and treatment. Therefore, the present invention should be construed as limited only by the appended claims.

We claim:

1. A method for diagnosis of a region of interest in a patient, the method comprising:
   (a) causing an oxy/deoxyhemoglobin shift in the region of interest using an ultrasound signal;
   (b) performing optical spectroscopy on the region of interest to obtain a ratio of optical absorption values at different wavelengths, a change of the ratio over time representing the oxy/deoxyhemoglobin shift: and
   (c) determining whether the region of interest contains tumor tissue by determining whether the ratio obtained in step (b) correlates with the ultrasound signal used in step (a), wherein a correlation between the ratio and the ultrasound signal is higher in a non-tumor case than in a tumor case.

2. The method of claim 1, wherein the region of interest is in a breast of the patient.

3. The method of claim 2, wherein step (b) is performed with an instrument while the instrument is held stationary relative to the region of interest.

4. The method of claim 3, wherein the instrument comprises an ultrasound transducer and an ultrasound probe, and wherein the ultrasound transducer and the ultrasound probe are moved within the instrument while the instrument is held stationary relative to the region of interest and while step (b) is performed.

5. The method of claim 1, wherein the region of interest is in a prostate of the patient.

6. The method of claim 5, wherein:
   step (a) is performed with an ultrasound probe; and
   step (b) is performed with an optical fiber probe inserted into a urethra of the patient.

7. The method of claim 6, wherein the ultrasound probe is inserted into a rectum of the patient.

8. The method of claim 6, wherein the ultrasound probe is applied to an abdominal wall of the patient.

9. The method of claim 1, wherein step (a) is performed using a stationary ultrasound wave.

10. The method of claim 1, wherein step (a) is performed using a stationary ultrasound wave.

11. The method of claim 1, wherein the different wavelengths are 560 nm and 540 nm.

12. A system for diagnosis of a region of interest in a patient, the system comprising:
   (a) an ultrasound device configured to cause an oxy/deoxyhemoglobin shift in the region of interest using an ultrasound signal; and
   (b) a diagnostic device configured to perform optical spectroscopy on the region of interest to obtain a ratio of optical absorption values at different wavelengths, a change of the ratio over time representing the oxy/deoxyhemoglobin shift, and configured to determine whether the region of interest contains tumor tissue by determining whether the ratio correlates with the ultrasound signal, wherein the diagnostic device is configured to take into account that a correlation between the ratio and the ultrasound signal is higher in a non-tumor case than in a tumor case; and
   (c) wherein the diagnostic device includes a computer display comprising a display area for tumor correlation and a display area for non-tumor correlation, said display device displaying at least one of the correlations for non-tumor tissue and for tumor tissue as a correlation metric indicative of the presence of tumor or non-tumor tissue at the region of interest.

13. The system of claim 12, further comprising a holding member configured to hold the system stationary relative to the region of interest.

14. The system of claim 13, wherein the ultrasound device comprises an ultrasound transducer and an ultrasound probe, and wherein the ultrasound transducer and the ultrasound probe are movable within the ultrasound device while the system is held stationary relative to the region of interest.

15. The system of claim 12, wherein the diagnostic device comprises an optical her probe for insertion into a urethra of the patient.

16. The system of claim 15, wherein the ultrasound device is configured to be inserted into a rectum of the patient.

17. The system of claim 15, wherein the ultrasound device is configured to be applied to an abdominal wall of the patient.

18. The system of claim 12, wherein the ultrasound device causes the blood stasis oxy/deoxyhemoglobin shift in the region of interest using a stationary ultrasound wave.

19. The system of claim 12, wherein the different wavelengths are 560 nm and 540 nm.

* * * * *